(12) United States Patent
Pahutski, Jr.

(10) Patent No.: US 8,895,738 B2
(45) Date of Patent: Nov. 25, 2014

(54) MESOIONIC PYRIDO [1, 2-A] PYRIMIDINE PESTICIDES

(75) Inventor: Thomas Francis Pahutski, Jr., Elkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/876,636

(22) PCT Filed: Dec. 22, 2011

(86) PCT No.: PCT/US2011/066798
§ 371 (c)(1),
(2), (4) Date: Mar. 28, 2013

(87) PCT Pub. No.: WO2012/092115
PCT Pub. Date: Jul. 5, 2012

(65) Prior Publication Data
US 2013/0190171 A1    Jul. 25, 2013

Related U.S. Application Data

(60) Provisional application No. 61/427,855, filed on Dec. 29, 2010, provisional application No. 61/550,675, filed on Oct. 24, 2011.

(51) Int. Cl.
*C07D 471/04* (2006.01)
*A01N 43/90* (2006.01)

(52) U.S. Cl.
CPC ............. *A01N 43/90* (2013.01); *C07D 471/04* (2013.01)
USPC ............................ 544/333; 546/304; 564/363

(58) Field of Classification Search
USPC .................. 424/405; 504/100, 136, 204, 243; 514/259.1, 259.41, 259.5; 544/253, 544/282, 284, 287, 333
See application file for complete search history.

(56) References Cited

U.S. PATENT DOCUMENTS

| 8,552,007 | B2 * | 10/2013 | Holyoke et al. | 514/259.4 |
| 2012/0115722 | A1 * | 5/2012 | Holyoke et al. | 504/100 |
| 2012/0122679 | A1 * | 5/2012 | Zhang et al. | 504/100 |
| 2012/0122680 | A1 * | 5/2012 | Holyoke et al. | 504/100 |
| 2012/0277100 | A1 * | 11/2012 | Zhang et al. | 504/100 |
| 2013/0338002 | A1 | 12/2013 | Holyoke, Jr. et al. | |

FOREIGN PATENT DOCUMENTS

WO     2012106495 A1     8/2012

OTHER PUBLICATIONS

U.S. Appl. No. 13/967,629 Office Action dated Jan. 21, 2014.

* cited by examiner

*Primary Examiner* — Jane C Oswecki
(74) *Attorney, Agent, or Firm* — Roman Kucharczyk

(57) ABSTRACT

Disclosed are compounds of Formula 1,

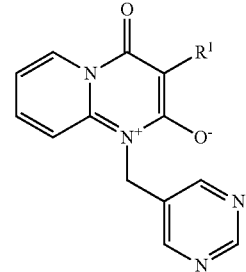

wherein
  $R^1$ is phenyl or pyridinyl, each optionally substituted with Q and up to 3 substituents independently selected from $R^2$;
  each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio; and
  Q is phenyl or pyridinyl, each optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Also disclosed are compositions containing the compounds of Formula 1 and methods for controlling an invertebrate pest comprising contacting the invertebrate pest or its environment with a biologically effective amount of a compound or a composition of the invention. Further disclosed are methods for increasing vigor of a crop plant comprising contacting the crop plant, the seed from which the crop plant is grown or the locus of the crop plant with a biologically effective amount of a compound or composition of the invention.

2 Claims, No Drawings

MESOIONIC PYRIDO [1, 2-A] PYRIMIDINE PESTICIDES

FIELD OF THE INVENTION

This invention relates to certain pyrimidinium compounds, their compositions suitable for agronomic and nonagronomic uses, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

PCT Patent Publication WO 09/099,929 discloses certain mesoionic pyrimidinium compounds of Formula i as insecticides

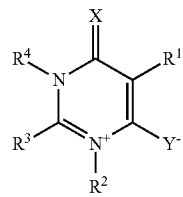

i wherein, inter alia, X and Y are O, $R^1$ is substituted phenyl, $R^2$ is $CH_2Q$ and Q is an optionally substituted 5- or 6-membered heteroaromatic ring, and $R^3$ and $R^4$ are taken together to form an optionally substituted 6-membered ring.

SUMMARY OF THE INVENTION

This invention is directed to compounds of Formula 1, compositions containing them and their use for controlling invertebrate pests:

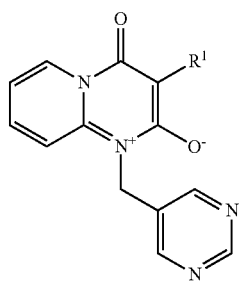

1 wherein
$R^1$ is phenyl or pyridinyl, each optionally substituted with Q and up to 3 substituents independently selected from $R^2$;

each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio; and
Q is phenyl or pyridinyl, each optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

This invention provides a composition comprising a compound of Formula 1 and at least one additional component selected from the group consisting of surfactants, solid diluents and liquid diluents. In one embodiment, this invention also provides a composition for controlling an invertebrate pest comprising a compound of Formula 1 and at least one additional component selected from the group consisting of surfactants, solid diluents and liquid diluents, said composition further comprising at least one additional biologically active compound or agent.

This invention also provides a method for controlling an invertebrate pest comprising contacting the invertebrate pest or its environment with a biologically effective amount of a compound of Formula 1 (e.g., as a composition described herein). This invention also relates to such method wherein the invertebrate pest or its environment is contacted with a composition comprising a biologically effective amount of a compound of Formula 1 and at least one additional component selected from the group consisting of surfactants, solid diluents and liquid diluents, said composition optionally further comprising a biologically effective amount of at least one additional biologically active compound or agent.

This invention also provides a method for controlling an invertebrate pest comprising contacting the invertebrate pest or its environment with a biologically effective amount of any of the aforesaid compositions wherein the environment is a plant.

This invention also provides a method for controlling an invertebrate pest comprising contacting the invertebrate pest or its environment with a biologically effective amount of any of the aforesaid compositions wherein the environment is a seed.

This invention also provides a method for protecting a seed from an invertebrate pest comprising contacting the seed with a biologically effective amount of a compound of Formula 1 (e.g., as a composition described herein). This invention also relates to the treated seed (i.e. seed contacted with a compound of Formula 1).

This invention also provides a method for increasing vigor of a crop plant comprising contacting the crop plant, the seed from which the crop plant is grown or the locus (e.g., growth medium) of the crop plant with a biologically effective amount of a compound of Formula 1 (e.g., as a composition described herein).

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods, nematodes and helminths of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes members of the phylum Nematoda, such as phytophagous nematodes and helminth nematodes parasitizing animals. The term "helminth" includes all of the parasitic worms, such as roundworms (phylum Nematoda), heartworms (phylum Nematoda, class Secernentea), flukes (phylum Platyhelminthes, class Tematoda), acanthocephalans (phylum Acanthocephala), and tapeworms (phylum Platyhelminthes, class Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of maize or corn, soybeans and other legumes, rice, cereal (e.g., wheat, oats, barley, rye and rice), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (e.g., berries and cherries) and other specialty crops (e.g., canola, sunflower and olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "crop vigor" refers to rate of growth or biomass accumulation of a crop plant. An "increase in vigor" refers to an increase in growth or biomass accumulation in a crop plant relative to an untreated control crop plant. The term "crop yield" refers to the return on crop material, in terms of both quantity and quality, obtained after harvesting a crop plant. An "increase in crop yield" refers to an increase in crop yield relative to an untreated control crop plant.

The term "biologically effective amount" refers to the amount of a biologically active compound (e.g., a compound of Formula 1) sufficient to produce the desired biological effect when applied to (i.e. contacted with) an invertebrate pest to be controlled or its environment, or to a plant, the seed from which the plant is grown, or the locus of the plant (e.g., growth medium) to protect the plant from injury by the invertebrate pest or for other desired effect (e.g., increasing plant vigor).

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

In the above recitations, the term "alkyl", used either alone or in compound words such as "haloalkyl" includes straight-chain or branched alkyl, such as methyl, ethyl, n-propyl, i-propyl, or the different butyl isomers.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $CF_3$, $CH_2Cl$, $CH_2CF_3$ and $CCl_2CF_3$. The terms "haloalkoxy" and "haloalkylthio" are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

"Alkoxy" includes, for example, methoxy, ethoxy, n-propoxy, isopropoxy and the different butoxy isomers.

The term "alkylthio" includes straight-chain or branched alkylthio moieties such as methylthio, ethylthio, and the different propylthio and butylthio isomers.

The total number of carbon atoms in a substituent group is indicated by the "$C_i$-$C_j$" prefix where i and j are numbers from 1 to 4. For example, $C_1$-$C_4$ alkyl designates methyl through butyl.

When a radical is optionally substituted with listed substituents with the number of substituents stated (e.g., "up to 3"), then the radical may be unsubstituted or substituted with a number of substituents ranging up to the high number stated (e.g., "3"), and the attached substituents are independently selected from the substituents listed.

The number of optional substituents may be restricted by an expressed limitation. For example, the phrase "optionally substituted with up to 3 substituents independently selected from $R^2$" means that 0, 1, 2 or 3 substituents can be present (if the number of potential connection points allows). When a range specified for the number of substituents exceeds the number of positions available for substituents on a ring, the actual higher end of the range is recognized to be the number of available positions.

The compounds of Formula 1 are mesoionic inner salts. "Inner salts", also known in the art as "zwitterions", are electrically neutral molecules but carry formal positive and negative charges on different atoms in each valence bond structure according to valence bond theory. Furthermore the molecular structure of the compounds of Formula 1 can be represented by the six valence bond structures shown below, each placing the formal positive and negative charges on different atoms. Because of this resonance, the compounds of Formula 1 are also described as "mesoionic". Although for sake of simplicity, the molecular structure of Formula 1 is depicted as a single valence bond structure herein, this particular valence bond structure is to be understood as representative of all six valence bond structures (depicted following this paragraph) relevant to bonding in molecules of compounds of Formula 1. Therefore reference to Formula 1 herein relates to all six applicable valence bond structures and other (e.g., molecular orbital theory) structures unless otherwise specified.

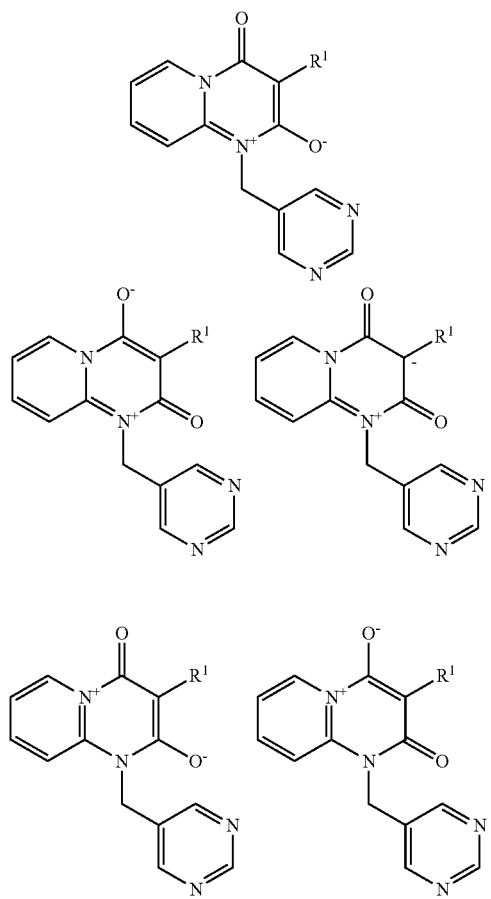

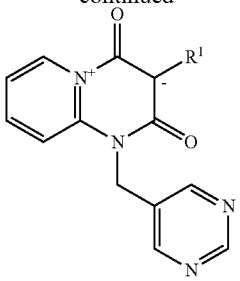

Compounds of this invention can exist as one or more conformational isomers due to restricted bond rotation caused by steric hinderance. For example, a compound of Formula 1 wherein $R^1$ is phenyl substituted in the ortho-position with a sterically demanding alkyl group (e.g., isopropyl) may exist as two rotamers due to restricted rotation about the $R^1$-pyrimidinium ring bond. This invention comprises mixtures of conformational isomers. In addition, this invention includes compounds that are enriched in one conformer relative to others.

Compounds selected from Formula 1 typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of invertebrate pests and animal parasites (i.e. are suitable for animal health use). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Embodiments of the present invention as described in the Summary of the Invention include those described below. In the following Embodiments reference to "a compound of Formula 1" includes the definitions of substituents specified in the Summary of the Invention unless further defined in the Embodiments.

Embodiment 1

A compound of Formula 1 wherein $R^1$ is phenyl optionally substituted with Q and up to 3 substituents independently selected from $R^2$.

Embodiment 1a

A compound of Embodiment 1 wherein $R^1$ is phenyl optionally substituted with up to 3 substituents independently selected from $R^2$.

Embodiment 2

A compound of Formula 1 wherein $R^1$ is pyridinyl optionally substituted with Q and up to 3 substituents independently selected from $R^2$.

Embodiment 2a

A compound of Embodiment 2 wherein $R^1$ is pyridinyl optionally substituted with up to 3 substituents independently selected from $R^2$.

Embodiment 3

A compound of Formula 1 or any one of Embodiments 1-2a wherein each $R^2$ is independently halogen, $C_1$-$C_4$ alkyl, $C_1$-$C_4$ haloalkyl, $C_1$-$C_4$ alkoxy or $C_1$-$C_4$ haloalkoxy.

Embodiment 3a

A compound of Embodiment 3 wherein each $R^2$ is independently halogen, $C_1$-$C_2$ alkyl, $C_1$-$C_2$ haloalkyl, $C_1$-$C_2$ alkoxy or $C_1$-$C_2$ haloalkoxy.

Embodiment 3b

A compound of Embodiment 3 wherein each $R^2$ is independently halogen.

Embodiment 3c

A compound of Embodiment 3 wherein each $R^2$ is independently $C_1$-$C_4$ alkyl.

Embodiment 3d

A compound of Embodiment 3 wherein each $R^2$ is independently $C_1$-$C_4$ haloalkyl.

Embodiment 3e

A compound of Embodiment 3 wherein each $R^2$ is independently $C_1$-$C_4$ alkoxy.

Embodiment 3f

A compound of Embodiment 3 wherein each $R^2$ is independently $C_1$-$C_4$ haloalkoxy.

Embodiment 4

A compound of Formula 1 or any one of Embodiments 1, 2 and 3-3f wherein Q is phenyl optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 4a

A compound of Formula 1 or any one of Embodiments 1, 2 and 3-3f wherein Q is pyridinyl optionally substituted with up to 4 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 4b

A compound of Embodiment 4 wherein Q is phenyl optionally substituted with up to 3 substituents independently selected from the group consisting of cyano and $C_1$-$C_4$ alkyl.

Embodiment 5

A compound of Formula 1 wherein $R^1$ is phenyl substituted with up to 2 substituents independently selected from the group consisting of halogen, $C_1$-$C_4$ haloalkyl and $C_1$-$C_4$ haloalkoxy.

Embodiment 6

A compound of Formula 1 wherein $R^1$ is phenyl substituted with halogen, $C_1$-$C_4$ haloalkyl or $C_1$-$C_4$ haloalkoxy.

Embodiment 7

A compound of Formula 1 wherein $R^1$ is phenyl substituted with $C_1$-$C_4$ haloalkyl or $C_1$-$C_4$ haloalkoxy.

Embodiments of this invention, including Embodiments 1-7 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-7 above as well as any other embodiments described herein, and any combination thereof, pertain to the compositions and methods of the present invention.

Combinations of Embodiments 1-7 are illustrated by:

Embodiment A

A compound of Formula 1 wherein
$R^1$ is phenyl optionally substituted with Q and up to 3 substituents independently selected from $R^2$; and
Q is phenyl or pyridinyl, each optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment B

A compound of Embodiment A wherein
$R^1$ is phenyl optionally substituted with up to 3 substituents independently selected from the group consisting of halogen, $C_1$-$C_4$ alkyl, $C_1$-$C_4$ haloalkyl, $C_1$-$C_4$ alkoxy and $C_1$-$C_4$ haloalkoxy.

Specific embodiments include compounds of Formula 1 selected from the group consisting of:
2-hydroxy-4-oxo-3-phenyl-1-(5-pyrimidinylmethyl)-4H-pyrido[1,2-a]pyrimidinium inner salt (i.e. compound 1 of Index Table A);
3-(4-fluorophenyl)-2-hydroxy-4-oxo-1-(5-pyrimidinylmethyl)-4H-pyrido[1,2-a]pyrimidinium inner salt (i.e. compound 2 of Index Table A);
2-hydroxy-4-oxo-1-(5-pyrimidinylmethyl)-3-[3-(trifluoromethyl)phenyl]-4H-pyrido[1,2-a]pyrimidinium inner salt (i.e. compound 3 of Index Table A);
2-hydroxy-3-(2-methoxyphenyl)-4-oxo-1-(5-pyrimidinylmethyl)-4H-pyrido[1,2-a]pyrimidinium inner salt (i.e. compound 4 of Index Table A);
2-hydroxy-3-(3-methoxyphenyl)-4-oxo-1-(5-pyrimidinylmethyl)-4H-pyrido[1,2-a]pyrimidinium inner salt (i.e. compound 5 of Index Table A);
3-(2,4-difluorophenyl)-2-hydroxy-4-oxo-1-(5-pyrimidinylmethyl)-4H-pyrido[1,2-a]pyrimidinium inner salt (i.e. compound 6 of Index Table A);
2-hydroxy-4-oxo-1-(5-pyrimidinylmethyl)-3-[3-(trifluoromethoxy)phenyl]-4H-pyrido[1,2-a]pyrimidinium inner salt (i.e. compound 7 of Index Table A);
3-(2-bromophenyl)-2-hydroxy-4-oxo-1-(5-pyrimidinylmethyl)-4H-pyrido[1,2-a]pyrimidinium inner salt (i.e. compound 8 of Index Table A);
3-(2-fluorophenyl)-2-hydroxy-4-oxo-1-(5-pyrimidinylmethyl)-4H-pyrido[1,2-a]pyrimidinium inner salt (i.e. compound 9 of Index Table A);
3-[2-fluoro-5-(trifluoromethyl)phenyl]-2-hydroxy-4-oxo-1-(5-pyrimidinylmethyl)-4H-pyrido[1,2-a]pyrimidinium inner salt (i.e. compound 10 of Index Table A);
2-hydroxy-3-(3-methylphenyl)-4-oxo-1-(5-pyrimidinylmethyl)-4H-pyrido[1,2-a]pyrimidinium inner salt (i.e. compound 11 of Index Table A);
3-[4-fluoro-3-(trifluoromethyl)phenyl]-2-hydroxy-4-oxo-1-(5-pyrimidinylmethyl)-4H-pyrido[1,2-a]pyrimidinium inner salt (i.e. compound 12 of Index Table A);
3-(4-chloro-2-fluorophenyl)-2-hydroxy-4-oxo-1-(5-pyrimidinylmethyl)-4H-pyrido[1,2-a]pyrimidinium inner salt (i.e. compound 13 of Index Table A);
3-(2-chlorophenyl)-2-hydroxy-4-oxo-1-(5-pyrimidinylmethyl)-4H-pyrido[1,2-a]pyrimidinium inner salt(i.e. compound 14 of Index Table A);
3-[3-chloro-5-(trifluoromethyl)phenyl]-2-hydroxy-4-oxo-1-(5-pyrimidinylmethyl)-4H-pyrido[1,2-a]pyrimidinium inner salt (i.e. compound 15 of Index Table A);
3-(3,5-dichlorophenyl)-2-hydroxy-4-oxo-1-(5-pyrimidinylmethyl)-4H-pyrido[1,2-a]pyrimidinium inner salt (i.e. compound 16 of Index Table A);
3-(3,5-dichloro-4-fluorophenyl)-2-hydroxy-4-oxo-1-(5-pyrimidinylmethyl)-4H-pyrido[1,2-a]pyrimidinium inner salt (i.e. compound 17 of Index Table A);
3-(4'-cyano-5,2'-dimethyl[1,1'-biphenyl]-3-yl)-2-hydroxy-4-oxo-1-(5-pyrimidinylmethyl)-4H-pyrido[1,2-a]pyrimidinium inner salt (i.e. compound 18 of Index Table A); and
3-(3-chlorophenyl)-2-hydroxy-4-oxo-1-(5-pyrimidinylmethyl)-4H-pyrido[1,2-a]pyrimidinium inner salt(i.e. compound 19 of Index Table A).

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a compound (i.e. in a biologically effective amount) of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent (i.e. in a biologically effective amount).

Embodiments of the invention also include a composition comprising a compound of any of the preceding Embodiments in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a compound (i.e. in a biologically effective amount) of any of the preceding Embodiments and a propellant. Embodiments of the invention further include a bait composition for controlling an invertebrate pest comprising a compound (i.e. in a biologically effective amount) of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include methods for controlling an invertebrate pest comprising contacting the invertebrate pest or its environment with a biologically effective amount of a compound of Formula 1 (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1 and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

Embodiments of the invention also include any of the preceding embodiments wherein the invertebrate pest is an arthropod. Embodiments of the invention also include any of the preceding embodiments wherein the arthropod is selected from the group consisting of insects, mites, spiders, scorpions, centipedes, millipedes, pill bugs and symphylans. Embodiments of the invention also include any of the preceding embodiments wherein the arthropod is an insect. Embodiments of the invention also include any of the preceding embodiments wherein the insect is in the order Hemiptera. Embodiments of the invention also include any of the preceding embodiments wherein the insect is a planthopper. Embodiments of the invention also include any of the preceding embodiments wherein the insect is a planthopper in the family Delphacidae. Embodiments of the invention also include any of the preceding embodiments wherein the insect is a leafhopper. Embodiments of the invention also include any of the preceding embodiments wherein the insect is a leafhopper in the family Cicadellidae.

Embodiments of the invention also include any of the preceding embodiments wherein the invertebrate pest is a gastropod. Embodiments of the invention also include any of the preceding embodiments wherein the gastropod is selected from the group consisting of snails, slugs and other Stylommatophora.

Embodiments of the invention also include any of the preceding embodiments wherein the invertebrate pest is a nematode. Embodiments of the invention also include any of the preceding embodiments wherein the nematode is selected from phytophagous nematodes.

Embodiments of the invention also include any of the preceding embodiments wherein the invertebrate pest is a helminth. Embodiments of the invention also include any of the preceding embodiments wherein the helminth is selected from the group consisting of roundworms, heartworms, flukes, acanthocephalans and tapeworms.

Embodiments of the invention also include embodiments pertaining to the method for increasing vigor of a crop plant disclosed in the Summary of the Invention wherein the compound of Formula 1 (e.g., as a composition described herein) is selected from any one of Embodiments 1-4-b, A and B, and compounds specifically disclosed herein.

One or more of the following methods and variations as described in Schemes 1-13 can be used to prepare the compounds of Formula 1. The definition of $R^1$ in the compounds of Formulae 1-13 below are as defined above in the Summary of the Invention unless otherwise noted. Formulae 1a and 1b are various subsets of Formula 1, and all substituents for Formulae 1a and 1e are as defined above for Formula 1 unless otherwise indicated. Ambient or room temperature is defined as about 20-25° C.

Compounds of Formula 1 can be prepared by condensation of the compound of Formula 2 with optionally substituted malonic acids of Formula 3a in the presence of condensing agents as shown in Scheme 1. Condensing agents can be carbodiimides such as dicyclohexyl carbodiimide (see, for example, Koch, A. et al. *Tetrahedron* 2004, 60, 10011-10018) or other agents well known in the art to form amide bonds with or without activating agents such as N-hydroxybenzotriazole as described in *Science of Synthesis* 2005, 21, 17-25 and Tetrahedron 2005, 61, 10827-10852. This reaction is typically carried out in an inert organic solvent, such as dichloromethane or 1,2-dichloroethane, at temperatures from about 0 to about 80° C. for a period of 10 min to several days.

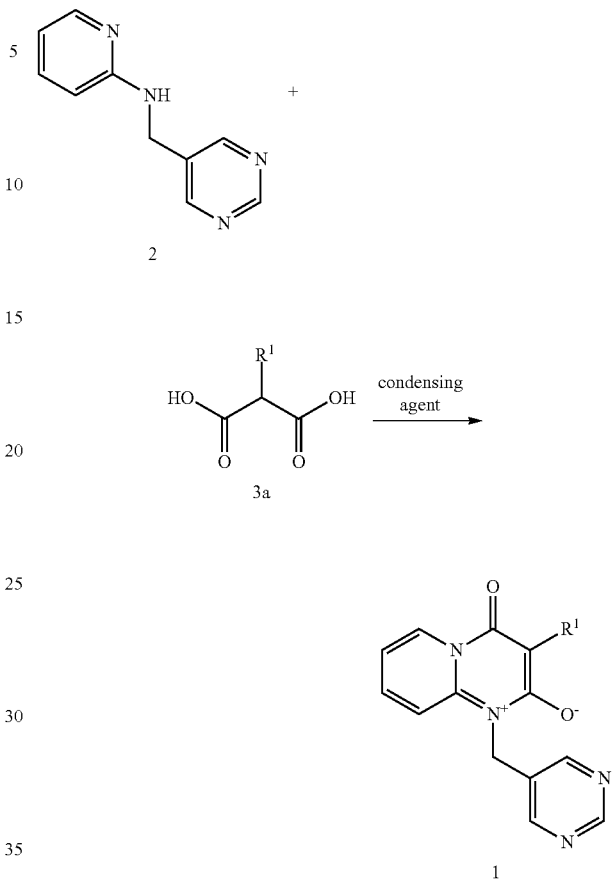

Scheme 1

Compounds of Formula 1 can also be prepared by the condensation of the compound of Formula 2 with malonic acid esters of Formula 3b wherein R is a $C_1$-$C_5$ alkyl group as shown in Scheme 2. These reactions can be performed neat or in the presence of inert solvents as described in *Bulletin of the Chemical Society of Japan* 1999, 72(3), 503-509. Inert solvents include, but are not limited to, high boiling hydrocarbons such as mesitylene, tetralin or cymene, or high boiling ethers such as diphenyl ether. Typical temperatures range from 50 to 250° C. Of note are temperatures from 150 to 200° C., which typically provide rapid reaction times and high yields. These reactions can also be performed in microwave reactors within the same temperature ranges. Typical reaction times range from 5 minutes to several hours.

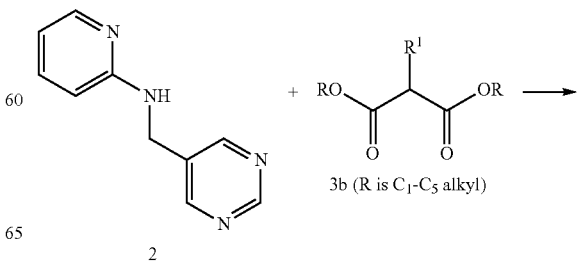

Scheme 2

3b (R is $C_1$-$C_5$ alkyl)

-continued

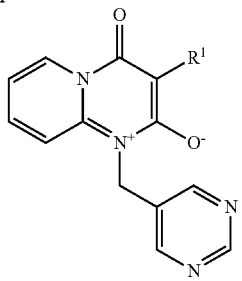

Compounds of Formula 3a can be prepared by a variety of methods known in the art, for example by base hydrolysis of compounds of Formula 3b.

Compounds of Formula 3b can be prepared by arylation of malonate esters (using compounds of formula $R^1X^1$ wherein $X^1$ is Cl, Br or I, examples of which are found in Tables I-24a, I-24-b and I-24c) catalyzed by palladium (*J. Org. Chem.* 2002, 67, 541-555) or copper (*Org. Lett.* 2002, 4, 269-272 and *Org. Lett.* 2005, 7, 4693-4695). Alternatively, compounds of Formula 3b can be prepared by the method shown in Scheme 2a (see, for example, *J. Med. Chem.* 1982, 25(6), 745-747).

Scheme 2a

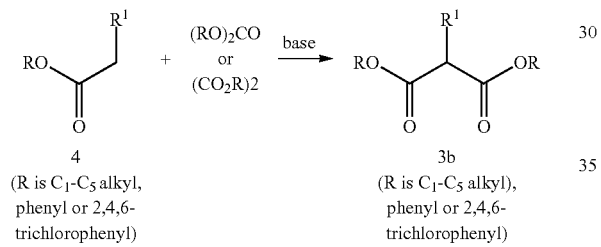

4
(R is $C_1$-$C_5$ alkyl, phenyl or 2,4,6-trichlorophenyl)

3b
(R is $C_1$-$C_5$ alkyl), phenyl or 2,4,6-trichlorophenyl)

Esters of Formula 4 can be prepared from the corresponding acids by methods well known in the art. The acids of Formula 4 wherein R is H (examples are listed in Table I-1) are readily prepared by methods known in the art, and many are commercially available.

Compounds of Formula 3b can also be prepared by the method shown in Scheme 2b. Reaction of nitriles of Formula 3g with dialkyl carbonates yields nitrile esters of Formula 3h, and subsequent acidic hydrolysis in the presence of an alcohol provides the compounds of Formula 3b (see, for example, *Helvetica Chimica Acta* 1991, 74(2), 309-314). The nitriles of Formula 3g are readily prepared by methods known in the art, and many are commercially available.

Scheme 2b

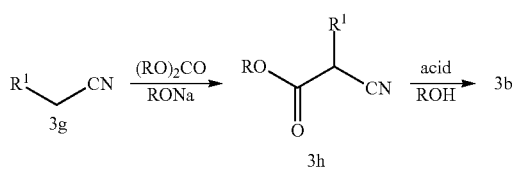

R is $C_1$-$C_5$ alkyl

Compounds of Formula 1 can also be prepared by treatment of the compound of Formula 2 with activated esters of Formula 3c wherein LvO is an activated leaving group as shown in Scheme 3. Examples of Lv preferred for ease of synthesis or reactivity are phenyl, 4-nitrophenyl or halogen-substituted phenyl (e.g., 2,4,6-trichlorophenyl, pentachlorophenyl or pentafluorophenyl) as described in *Archiv der Pharmazie* (Weinheim, Germany) 1991, 324, 863-866. Other activated esters are well known in the art and include, but are not limited to, N-hydroxysuccinimide esters (see, for example, *J. Am. Chem. Soc.* 2002, 124, 6872-6878). Typical temperatures range from 50 to 200° C. Of note are temperatures from 50 to 150° C., which typically provide rapid reaction times and high yields. These reactions can be performed with or without solvent, such as toluene, and in microwave reactors within the same temperature ranges. Typical reaction times range from 5 minutes to 2 hours.

Scheme 3

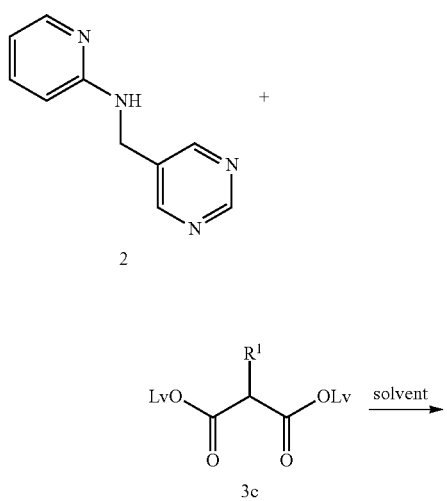

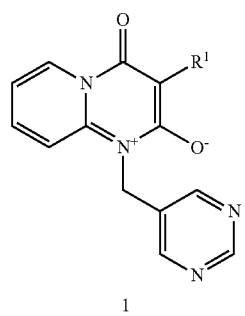

Compounds of the Formula 3c can be prepared, for example, from compounds of Formula 3a (see, for example, *J. Het. Chem.* 1980, 17, 337).

Compounds of Formula 1 can also be prepared by condensation of the compound of Formula 2 with compounds of Formula 3d or 3e, or by condensation of the compound of Formula 2 with mixtures of compounds of Formulae 3d and 3e as shown in Scheme 4. These reactions are typically performed in an inert solvent, such as dichloromethane, and optionally in the presence of two or more equivalents of an acid acceptor (see, for example, *Zeitschrift für Naturforschung, Teil B: Anorganische Chemie, Organische Chemie* 1982, 37B(2), 222-233). Typical acid acceptors include, but are not limited to, triethylamine, N,N-diisopropylethylamine, pyridine and substituted pyridines, and metal hydroxides, carbonates and bicarbonates.

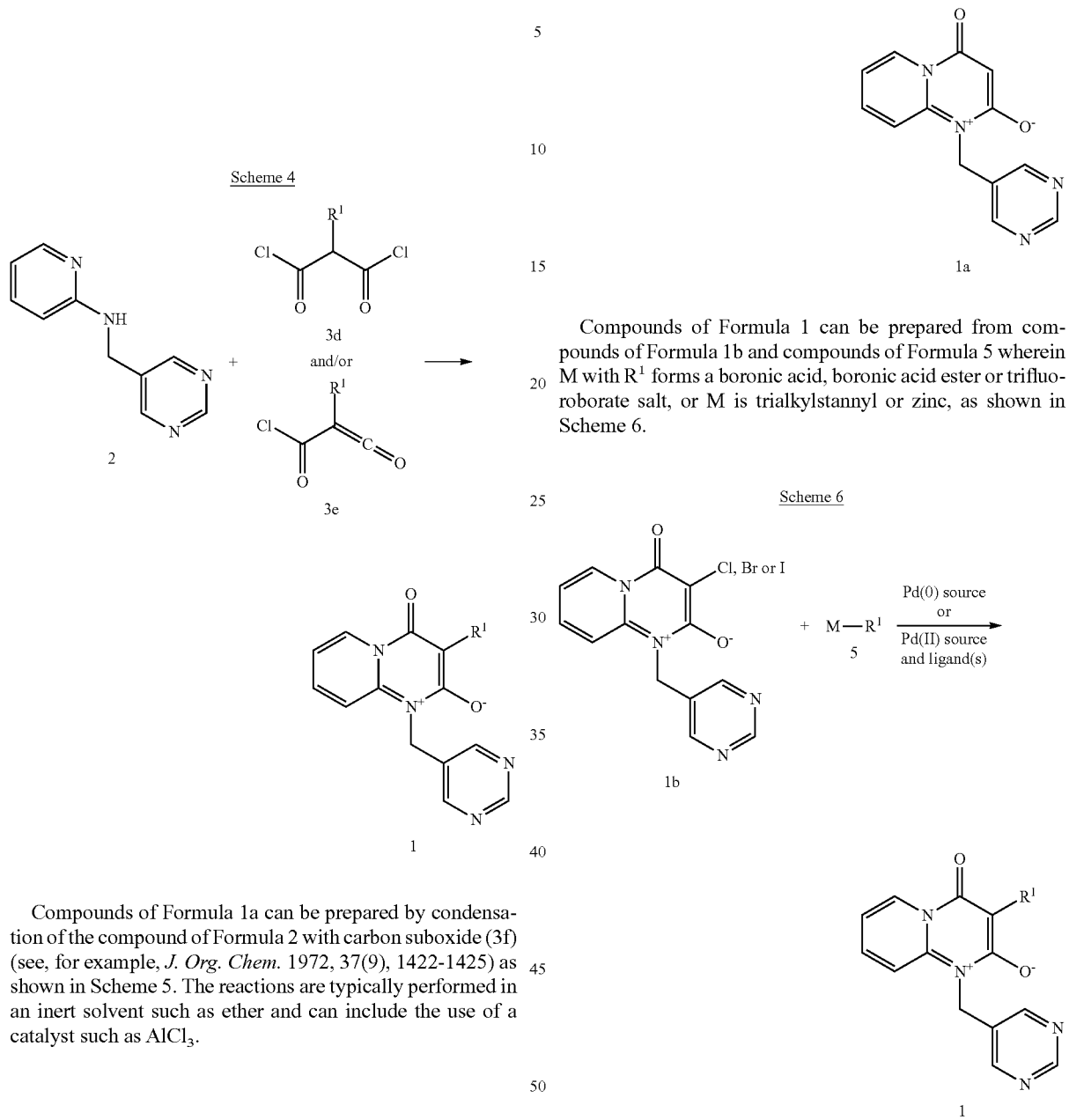

Compounds of Formula 1a can be prepared by condensation of the compound of Formula 2 with carbon suboxide (3f) (see, for example, *J. Org. Chem.* 1972, 37(9), 1422-1425) as shown in Scheme 5. The reactions are typically performed in an inert solvent such as ether and can include the use of a catalyst such as $AlCl_3$.

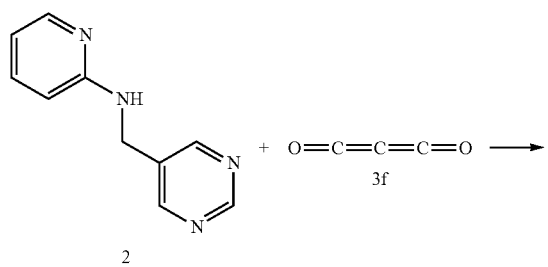

Compounds of Formula 1 can be prepared from compounds of Formula 1b and compounds of Formula 5 wherein M with $R^1$ forms a boronic acid, boronic acid ester or trifluoroborate salt, or M is trialkylstannyl or zinc, as shown in Scheme 6.

In a similar manner, compounds of Formula 1 wherein $R^1$ consists of two directly bonded aromatic rings (e.g., a phenyl ring bonded to a second phenyl ring, a phenyl ring bonded to a pyridinyl ring, or a pyridinyl ring bonded to a second pyridinyl ring) can be prepared by palladium-catalyzed coupling of the two appropriately substituted aromatic rings. These palladium-catalyzed couplings between an aromatic chloride, bromide or iodide and an aromatic boronic acid or ester, or an aromatic tin or zinc reagent, are well known and have been extensively described in the art. For example, see Scheme 6a, wherein a compound of Formula 13a or 13b is coupled with an appropriately substituted phenyl ring to provide the biphenyl compound of Formula 13c. M is as defined above for Scheme 6.

Scheme 6a

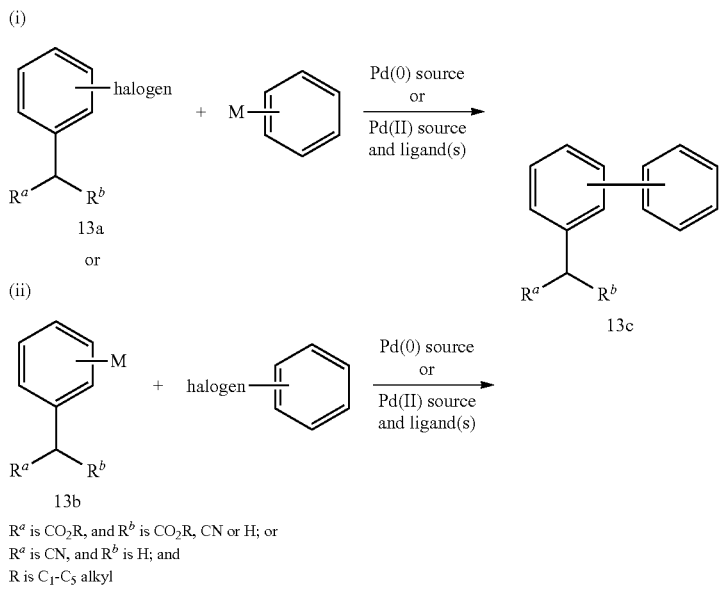

$R^a$ is $CO_2R$, and $R^b$ is $CO_2R$, CN or H; or
$R^a$ is CN, and $R^b$ is H; and
R is $C_1$-$C_5$ alkyl These coupling reactions are typically carried out in the presence of a palladium catalyst and a base optionally under an inert atmosphere. The palladium catalysts used for these coupling reactions typically comprises palladium in a formal oxidation state of either 0 (i.e. Pd(0)) or 2 (i.e. Pd(II)). A wide variety of such palladium-containing compounds and complexes are useful as catalysts for these reactions. Examples of palladium-containing compounds and complexes useful as catalysts in the methods include $PdCl_2(PPh_3)_2$ (bis(triphenylphosphine)palladium (II) dichloride), $Pd(PPh_3)_4$ (tetrakis(triphenylphosphine)-palladium(0)), $Pd(C_5H_7O_2)_2$ (palladium(II) acetylacetonate), $Pd_2(dba)_3$ (tris(dibenzylideneacetone)dipalladium(0)), and [1,1'-bis(diphenylphosphino)ferrocene]dichloropalladium(II). These coupling methods are generally conducted in a liquid phase, and therefore the palladium catalyst preferably has good solubility in the liquid phase. Useful solvents include, for example, water, ethers such as 1,2-dimethoxyethane, amides such as N,N-dimethylacetamide, and non-halogenated aromatic hydrocarbons such as toluene.

The coupling methods can be conducted over a wide range of temperatures, ranging from about 25 to about 200° C. Of note are temperatures from about 60 to about 150° C., which typically provide fast reaction times and high product yields. The general methods and procedures for Stille, Negishi and Suzuki couplings with aryl iodides, bromides or chlorides and an aryl tin, aryl zinc or aryl boronic acid respectively are well known in the literature; see, for example, E. Negishi, *Handbook of Organopalladium Chemistry for Organic Synthesis*, Wiley-Interscience, 2002, New York, N.Y.

Compounds of Formula 1 can be prepared from compounds of Formula 1a (i.e. Formula 1 wherein $R^1$ is H) and compounds of Formula 6 wherein $X^1$ is Cl, Br or I (preferably Br or I) as shown in Scheme 7.

Scheme 7

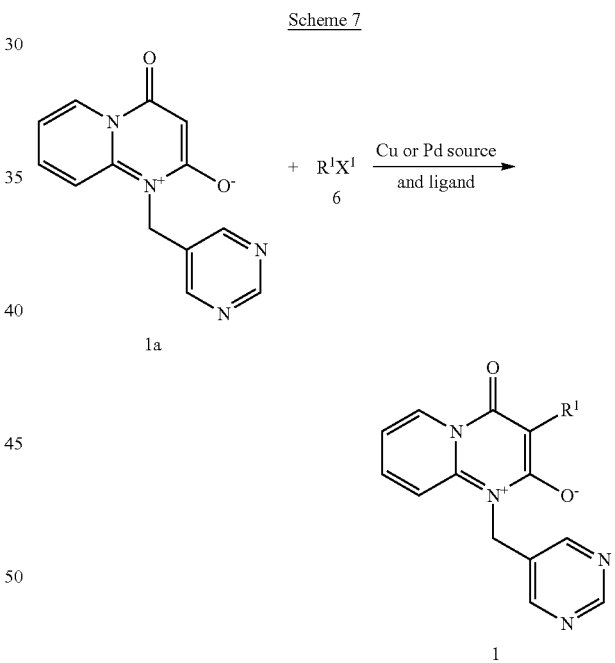

These reactions are typically carried out in the presence of a copper or palladium catalyst preferably under an inert atmosphere. The copper catalysts used for the present method typically comprise copper in metallic form (e.g., as a powder) or copper in a formal oxidation state of 1 (i.e. Cu(I)). Examples of copper-containing compounds useful as catalysts in the method of Scheme 7 include Cu, CuI, CuBr, CuCl. Examples of palladium-containing compounds useful as catalysts in the method of Scheme 7 include $Pd(OAc)_2$. Useful solvents for the method of Scheme 7 include, for example, ethers such as 1,4-dioxane, amides such as N,N-dimethylacetamide and dimethyl sulfoxide.

The method of Scheme 7 can be conducted over a wide range of temperatures from 25 to 200° C. Of note are temperatures from 40 to 150° C. The method of Scheme 7 can be conducted in the presence of a ligand. A wide variety of copper-binding compounds are useful as ligands for the present method. Examples of useful ligands include, but are not limited to, 1,10-phenanthroline, N,N-dimethylethylenediamine, L-proline and 2-picolinic acid. The general methods and procedures for copper-catalyzed Ullmann-type coupling reactions are well known in the literature; see, for example, Xie, Ma, et al. *Org. Lett.* 2005, 7, 4693-4695.

Compounds of Formula 1b can be prepared from compounds of Formula 1a by halogenation using, for example, liquid bromine or N-halosuccinimides of Formula 10 as shown in Scheme 11. Typically the reaction is performed in an inert solvent, more typically a halogenated solvent such as methylene chloride or 1,2-dichloroethane. The reaction is typically performed at temperatures from 0 to 80° C., more typically at ambient temperature.

Scheme 11

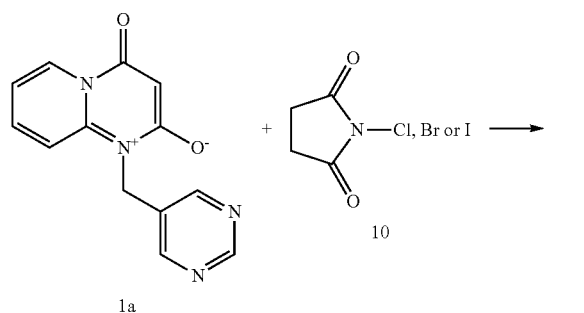

Compounds of Formula 1 can also be prepared by alkylation of compounds of Formula 11 using appropriately substituted alkylating agents and bases such as potassium carbonate as shown in Scheme 12 (see, for example, Kappe, T. et al. *Monatschefte fur Chemie* 1971, 102, 412-424 and Urban, M. G.; Arnold, W. *Helvetica Chimica Acta* 1970, 53, 905-922). Alkylating agents include, but are not limited to, alkyl chlorides, bromides, iodides and sulfonate esters. A wide variety of bases and solvents can be employed in the method of Scheme 12, and these bases and solvents are well known in the art.

Scheme 12

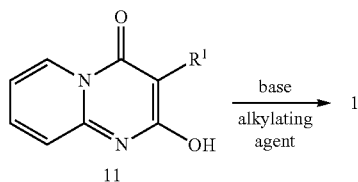

Compounds of Formula 11 can be prepared from 2-aminopyridine by methods analogous to those shown in Schemes 1 through 5.

As shown in Schemes 1-5, the compound of Formula 2 is an important intermediate useful in the preparation of compounds of Formula 1. The compound of Formula 2 is an embodiment of the present invention. A further embodiment of the present invention is the use of the compound of Formula 2 in the preparation of compounds of Formula 1.

One skilled in the art will recognize that the compound of Formula 2 can also be used as its acid-addition salt (e.g., hydrochloric salt or acetic acid salt) in the coupling methods of Schemes 1-5.

A particularly useful method for the preparation of the compound of Formula 2 is shown in Scheme 13. In the method of Scheme 13, 2-aminopyridine (2a) is protected with suitable protecting groups such as, but not limited to, tert-butoxycarbonyl, acetyl or formyl to form the intermediate of Formula 2b wherein PG is a protecting group. The compound of Formula 2b is then alkylated with a compound of Formula 12 (wherein X is a leaving group such as a halogen) to give an intermediate of Formula 2c. The protecting group is removed to provide the compound of Formula 2. Conditions for the formation and removal of protecting groups on an amine function are known in the literature (see, for example, Greene, T. W.; Wuts, P. G. M. *Protective Groups in Organic Synthesis*, 2nd ed.; Wiley: New York, 1991).

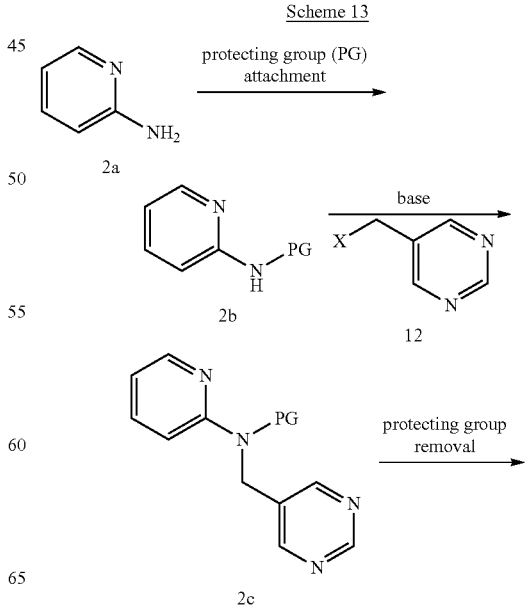

-continued

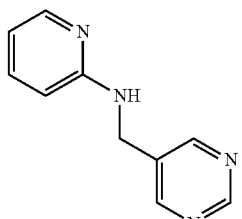

2

An alternative method for the preparation of the compound of Formula 2 is by the reductive amination of the appropriate carbonyl compound. This method is shown in Steps A and B of Synthesis Example 1.

Another alternative method for the preparation of the compound of Formula 2 is by the reaction of an appropriate amine with the halogen-substituted compound analogous to the compound of Formula 2a (i.e. Formula 2a wherein the amino group is replaced with halogen) in the presence of a copper or palladium catalyst.

Compounds of Formula 1 having $R^1$ substituents other than those particularly noted for Schemes 1 through 13 can be prepared by general methods known in the art of synthetic organic chemistry, including methods analogous to those described for Schemes 1 to 13.

Examples of intermediates useful in the preparation of compounds of this invention are shown in Tables I-1 through I-43. The following abbreviations are used in the Tables which follow: Me means methyl, Et means ethyl, Pr means propyl, Ph means phenyl, C(O)O(2,4,6-trichlorophenyl) means

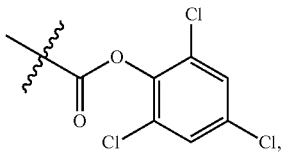

C(O)O(4-nitrophenyl) means

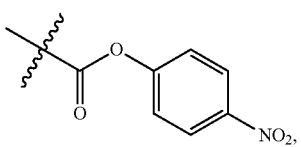 [SMILES: *C(=O)Oc1ccc([N+](=O)[O-])cc1]

and
C(O)(3-methyl-2-pyridinylamino) means

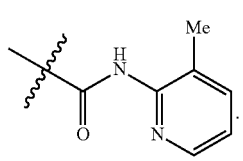 [SMILES: *C(=O)Nc1ncccc1C]

TABLE I-1

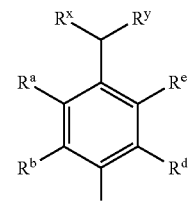

$R^x$ is C(O)OH; $R^y$ is H; $R^b$, $R^c$, $R^d$ and $R^e$ are H $R^a$

H
F
Cl
Br
I
cyano
Me
Et
Pr
i-Pr
t-Bu
$CF_3$
$CH_2F$
$CHF_2$
OMe
OEt
O-n-Pr
O-i-Pr
$OCF_3$
$OCHF_2$
$OCH_2CF_3$
$SCF_3$
$SCF_3$
$SCHF_2$
phenyl
2-fluorophenyl
3-chlorophenyl
3-($CF_3$)phenyl
3-fluorophenyl
3-cyanophenyl
3-($OCF_3$)phenyl
4-fluorophenyl
4-chlorophenyl
4-($CF_3$)phenyl
4-cyanophenyl
4-bromophenyl
6-chloro-3-pyridinyl
6-fluoro-3-pyridinyl
6-($CF_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-($CF_3$)phenyl
2,4-bis($CF_3$)phenyl
2-fluoro-4-bromophenyl
2-chloro-4-fluorophenyl
2-($CF_3$)-4-fluorophenyl
2-methyl-4-($CF_3$)phenyl
2-chloro-4-($CF_3$)phenyl
2-($CF_3$)-4-chlorophenyl
2,5-difluorophenyl
2-fluoro-5-($CF_3$)phenyl
2-fluoro-5-chlorophenyl
2,5-dichlorophenyl
2-fluoro-5-($OCF_3$)phenyl
2-chloro-5-($CF_3$)phenyl

TABLE I-1-continued

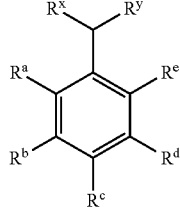

$R^x$ is C(O)OH; $R^y$ is H; $R^a$, $R^c$, $R^d$ and $R^e$ are H $R^b$

H
F
Cl
Br
I
cyano
Me
Et
Pr
i-Pr
t-Bu
$CF_3$
$CH_2F$
$CHF_2$
OMe
OEt
O-n-Pr
O-i-Pr
$OCF_3$
$OCHF_2$
$OCH_2CF_3$
$SCF_3$
$SCF_3$
$SCHF_2$
phenyl
2-fluorophenyl
3-chlorophenyl
3-($CF_3$)phenyl
3-fluorophenyl
3-cyanophenyl
3-($OCF_3$)phenyl
4-fluorophenyl
4-chlorophenyl
4-($CF_3$)phenyl
4-cyanophenyl
4-bromophenyl
6-chloro-3-pyridinyl
6-fluoro-3-pyridinyl
6-($CF_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-($CF_3$)phenyl
2,4-bis($CF_3$)phenyl
2-fluoro-4-bromophenyl
2-chloro-4-fluorophenyl
2-($CF_3$)-4-fluorophenyl
2-methyl-4-($CF_3$)phenyl
2-chloro-4-($CF_3$)phenyl
2-($CF_3$)-4-chlorophenyl
2,5-difluorophenyl
2-fluoro-5-($CF_3$)phenyl
2-fluoro-5-chlorophenyl
2,5-dichlorophenyl
2-fluoro-5-($OCF_3$)phenyl

TABLE I-1-continued

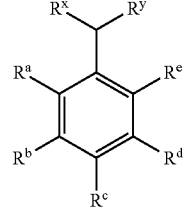

2-chloro-5-($CF_3$)phenyl $R^x$ is C(O)OH; $R^y$ is H; $R^a$, $R^b$, $R^d$ and $R^e$ are H $R^c$ H
F
Cl
Br
I
cyano
Me
Et
Pr
i-Pr
t-Bu
$CF_3$
$CH_2F$
$CHF_2$
OMe
OEt
O-n-Pr
O-i-Pr
$OCF_3$
$OCHF_2$
$OCH_2CF_3$
$SCF_3$
$SCF_3$
$SCHF_2$
phenyl
2-fluorophenyl
3-chlorophenyl
3-($CF_3$)phenyl
3-fluorophenyl
3-cyanophenyl
3-($OCF_3$)phenyl
4-fluorophenyl
4-chlorophenyl
4-($CF_3$)phenyl
4-cyanophenyl
4-bromophenyl
6-chloro-3-pyridinyl
6-fluoro-3-pyridinyl
6-($CF_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-($CF_3$)phenyl
2,4-bis($CF_3$)phenyl
2-fluoro-4-bromophenyl
2-chloro-4-fluorophenyl
2-($CF_3$)-4-fluorophenyl
2-methyl-4-($CF_3$)phenyl
2-chloro-4-($CF_3$)phenyl
2-($CF_3$)-4-chlorophenyl
2,5-difluorophenyl
2-fluoro-5-($CF_3$)phenyl
2-fluoro-5-chlorophenyl
2,5-dichlorophenyl TABLE I-1-continued

[Structure: phenyl ring with CH(R^x)(R^y) at top, R^a ortho, R^e ortho, R^b meta, R^d meta, R^c para]

2-fluoro-5-(OCF$_3$)phenyl
2-chloro-5-(CF$_3$)phenyl

R$^x$ is C(O)OH; R$^y$ is H; R$^a$ is F; R$^c$, R$^d$ and R$^e$ are H

R$^b$

H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl TABLE I-1-continued

[Structure: phenyl ring with CH(R^x)(R^y) at top, R^a ortho, R^e ortho, R^b meta, R^d meta, R^c para]

2,5-dichlorophenyl
2-fluoro-5-(OCF$_3$)phenyl
2-chloro-5-(CF$_3$)phenyl

R$^x$ is C(O)OH; R$^y$ is H; R$^a$ is F; R$^b$, R$^d$ and R$^e$ are H

R$^c$

H
F
Cl
Br
I
cyano
Me
Et
Pr
i-Pr
t-Bu
CF3
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl

TABLE I-1-continued

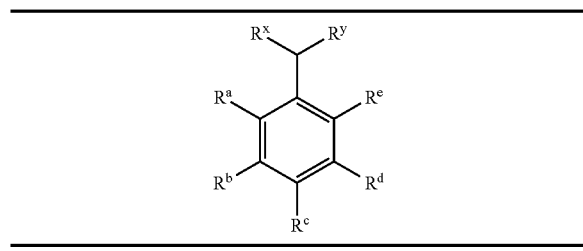

2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^a$ is F; R$^b$, R$^c$ and R$^e$ are H R$^d$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF3
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl

TABLE I-1-continued

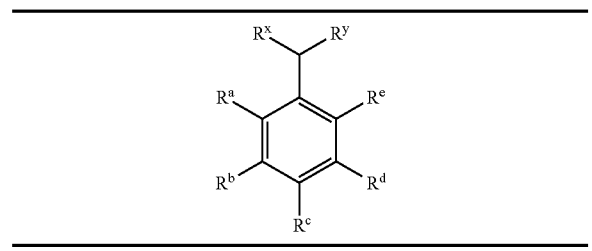

2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^a$ is F; R$^b$, R$^c$ and R$^d$ are H R$^e$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl

TABLE I-1-continued

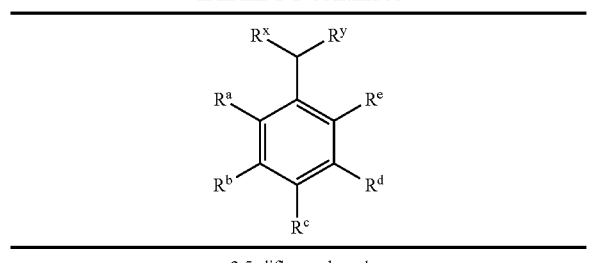

2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is Cl; $R^c$, $R^d$ and $R^e$ are H $R^b$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl

TABLE I-1-continued

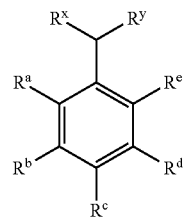

2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is Cl; $R^b$, $R^d$ and $R^e$ are H $R^c$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl

TABLE I-1-continued

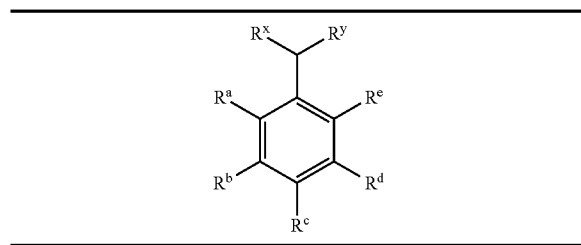

| | |
|---|---|
| 2-chloro-4-($CF_3$)phenyl | 2-methyl-4-($CF_3$)phenyl |
| 2-($CF_3$)-4-chlorophenyl | 2-chloro-4-($CF_3$)phenyl |
| 2,5-difluorophenyl | 2-($CF_3$)-4-chlorophenyl |
| 2-fluoro-5-($CF_3$)phenyl | 2,5-difluorophenyl |
| 2-fluoro-5-chlorophenyl | 2-fluoro-5-($CF_3$)phenyl |
| 2,5-dichlorophenyl | 2-fluoro-5-chlorophenyl |
| 2-fluoro-5-($OCF_3$)phenyl | 2,5-dichlorophenyl |
| 2-chloro-5-($CF_3$)phenyl | 2-fluoro-5-($OCF_3$)phenyl |
| | 2-chloro-5-($CF_3$)phenyl |

$R^x$ is C(O)OH; $R^y$ is H; $R^a$ is Cl; $R^b$, $R^c$ and $R^e$ are H

| $R^d$ | $R^e$ |
|---|---|
| H | H |
| F | F |
| Cl | Cl |
| Br | Br |
| I | I |
| cyano | cyano |
| Me | Me |
| Et | Et |
| Pr | Pr |
| i-Pr | i-Pr |
| t-Bu | t-Bu |
| $CF_3$ | $CF_3$ |
| $CH_2F$ | $CH_2F$ |
| $CHF_2$ | $CHF_2$ |
| OMe | OMe |
| OEt | OEt |
| O-n-Pr | O-n-Pr |
| O-i-Pr | O-i-Pr |
| $OCF_3$ | $OCF_3$ |
| $OCHF_2$ | $OCHF_2$ |
| $OCH_2CF_3$ | $OCH_2CF_3$ |
| $SCF_3$ | $SCF_3$ |
| $SCF_3$ | $SCF_3$ |
| $SCHF_2$ | $SCHF_2$ |
| phenyl | phenyl |
| 2-fluorophenyl | 2-fluorophenyl |
| 3-chlorophenyl | 3-chlorophenyl |
| 3-($CF_3$)phenyl | 3-($CF_3$)phenyl |
| 3-fluorophenyl | 3-fluorophenyl |
| 3-cyanophenyl | 3-cyanophenyl |
| 3-($OCF_3$)phenyl | 3-($OCF_3$)phenyl |
| 4-fluorophenyl | 4-fluorophenyl |
| 4-chlorophenyl | 4-chlorophenyl |
| 4-($CF_3$)phenyl | 4-($CF_3$)phenyl |
| 4-cyanophenyl | 4-cyanophenyl |
| 4-bromophenyl | 4-bromophenyl |
| 6-chloro-3-pyridinyl | 6-chloro-3-pyridinyl |
| 6-fluoro-3-pyridinyl | 6-fluoro-3-pyridinyl |
| 6-($CF_3$)-3-pyridinyl | 6-($CF_3$)-3-pyridinyl |
| 4,6-dichloro-3-pyridinyl | 4,6-dichloro-3-pyridinyl |
| 2-fluoro-6-chloro-3-pyridinyl | 2-fluoro-6-chloro-3-pyridinyl |
| 2,6-dichloro-3-pyridinyl | 2,6-dichloro-3-pyridinyl |
| 2-bromo-5-chloro-4-pyridinyl | 2-bromo-5-chloro-4-pyridinyl |
| 3-bromo-5-fluorophenyl | 3-bromo-5-fluorophenyl |
| 3-chloro-5-fluorophenyl | 3-chloro-5-fluorophenyl |
| 3-fluoro-4-chlorophenyl | 3-fluoro-4-chlorophenyl |
| 2,4-dichlorophenyl | 2,4-dichlorophenyl |
| 2,4-difluorophenyl | 2,4-difluorophenyl |
| 2-fluoro-4-cyanophenyl | 2-fluoro-4-cyanophenyl |
| 2-fluoro-4-chlorophenyl | 2-fluoro-4-chlorophenyl |
| 2-methyl-4-chlorophenyl | 2-methyl-4-chlorophenyl |
| 2-fluoro-4-($CF_3$)phenyl | 2-fluoro-4-($CF_3$)phenyl |
| 2,4-bis($CF_3$)phenyl | 2,4-bis($CF_3$)phenyl |
| 2-fluoro-4-bromophenyl | 2-fluoro-4-bromophenyl |
| 2-chloro-4-fluorophenyl | 2-chloro-4-fluorophenyl |
| 2-($CF_3$)-4-fluorophenyl | |

TABLE I-1-continued

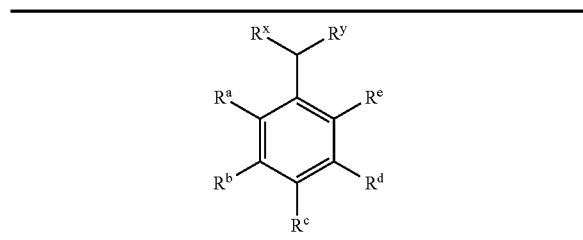

| 2-(CF₃)-4-fluorophenyl |
| 2-methyl-4-(CF₃)phenyl |
| 2-chloro-4-(CF₃)phenyl |
| 2-(CF₃)-4-chlorophenyl |
| 2,5-difluorophenyl |
| 2-fluoro-5-(CF₃)phenyl |
| 2-fluoro-5-chlorophenyl |
| 2,5-dichlorophenyl |
| 2-fluoro-5-(OCF₃)phenyl |
| 2-chloro-5-(CF₃)phenyl |

$R^x$ is C(O)OH; $R^y$ is H; $R^a$ is OMe; $R^c$, $R^d$ and $R^e$ are H $R^b$

H
F
Cl
Br
I
cyano
Me
Et
Pr
i-Pr
t-Bu
CF₃
CH₂F
CHF₂
OMe
OEt
O-n-Pr
O-i-Pr
OCF₃
OCHF₂
OCH₂CF₃
SCF₃
SCF₃
SCHF₂
phenyl
2-fluorophenyl
3-chlorophenyl
3-(CF₃)phenyl
3-fluorophenyl
3-cyanophenyl
3-(OCF₃)phenyl
4-fluorophenyl
4-chlorophenyl
4-(CF₃)phenyl
4-cyanophenyl
4-bromophenyl
6-chloro-3-pyridinyl
6-fluoro-3-pyridinyl
6-(CF₃)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF₃)phenyl
2,4-bis(CF₃)phenyl
2-fluoro-4-bromophenyl TABLE I-1-continued

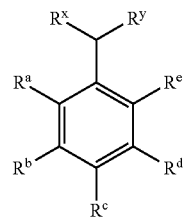

| 2-chloro-4-fluorophenyl |
| 2-(CF₃)-4-fluorophenyl |
| 2-methyl-4-(CF₃)phenyl |
| 2-chloro-4-(CF₃)phenyl |
| 2-(CF₃)-4-chlorophenyl |
| 2,5-difluorophenyl |
| 2-fluoro-5-(CF₃)phenyl |
| 2-fluoro-5-chlorophenyl |
| 2,5-dichlorophenyl |
| 2-fluoro-5-(OCF₃)phenyl |
| 2-chloro-5-(CF₃)phenyl |

$R^x$ is C(O)OH; $R^y$ is H; $R^a$ is OMe; $R^b$, $R^d$ and $R^e$ are H $R^c$

H
F
Cl
Br
I
cyano
Me
Et
Pr
i-Pr
t-Bu
CF₃
CH₂F
CHF₂
OMe
OEt
O-n-Pr
O-i-Pr
OCF₃
OCHF₂
OCH₂CF₃
SCF₃
SCF₃
SCHF₂
phenyl
2-fluorophenyl
3-chlorophenyl
3-(CF₃)phenyl
3-fluorophenyl
3-cyanophenyl
3-(OCF₃)phenyl
4-fluorophenyl
4-chlorophenyl
4-(CF₃)phenyl
4-cyanophenyl
4-bromophenyl
6-chloro-3-pyridinyl
6-fluoro-3-pyridinyl
6-(CF₃)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF₃)phenyl
2,4-bis(CF₃)phenyl TABLE I-1-continued

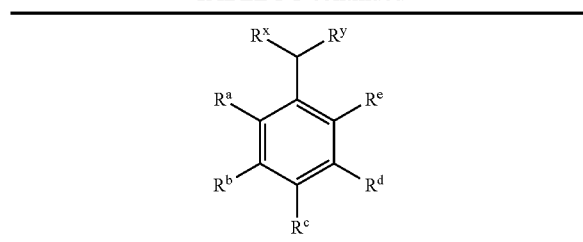

2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is OMe; $R^b$, $R^c$ and $R^e$ are H $R^d$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl TABLE I-1-continued

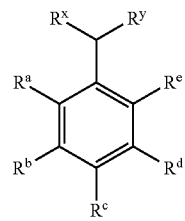

2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is OMe; $R^b$, $R^c$ and $R^d$ are H $R^e$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl TABLE I-1-continued

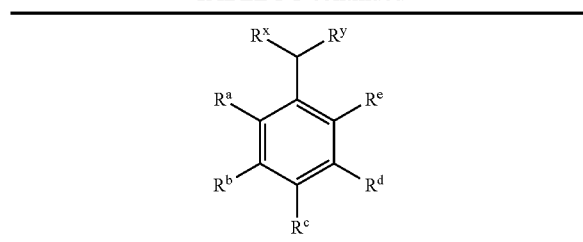

2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^a$ is Me; R$^c$, R$^d$ and R$^e$ are H R$^b$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl TABLE I-1-continued

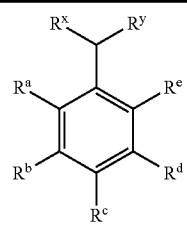

2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^a$ is Me; R$^b$, R$^d$ and R$^e$ are H R$^c$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl TABLE I-1-continued

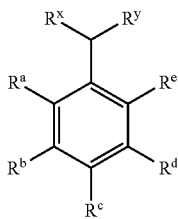

2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is Me; $R^b$, $R^c$ and $R^e$ are H $R^d$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl TABLE I-1-continued

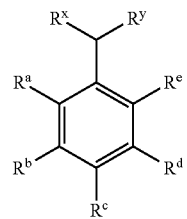

2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^a$ is Me; $R^b$, $R^c$ and $R^d$ are H $R^e$ H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl TABLE I-1-continued

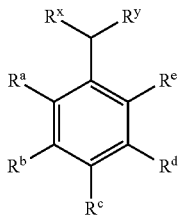

2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl

| $R^b$ |
|---|
| $R^x$ is C(O)OH; $R^y$ is H; $R^d$ is Cl; $R^a$, $R^c$ and $R^e$ are H |

H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl TABLE I-1-continued

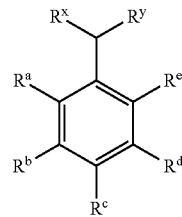

2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl
$R^x$ is C(O)OH; $R^y$ is H; $R^d$ is CF$_3$; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl TABLE I-1-continued

[Structure: benzene ring with substituents Rx, Ry on CH; Ra, Rb, Rc, Rd, Re on ring]

2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl

---

$R^d$ $R^x$ is C(O)OH; $R^y$ is H; $R^b$ is Br; $R^a$, $R^c$ and $R^e$ are H

H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl

---

TABLE I-1-continued 2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^b$ is OCF$_3$; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl TABLE I-1-continued

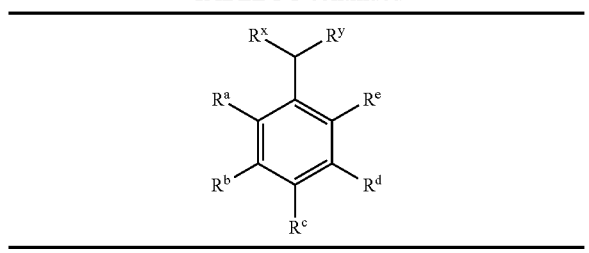

2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^b$ is OMe; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl TABLE I-1-continued

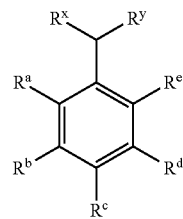

2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl $R^x$ is C(O)OH; $R^y$ is H; $R^b$ is F; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl TABLE I-1-continued

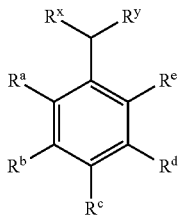

2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl
$R^x$ is C(O)OH; $R^y$ is H; $R^b$ is CN; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl TABLE I-1-continued

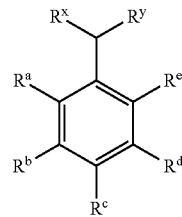

2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl
$R^x$ is C(O)OH; $R^y$ is H; $R^b$ is Me; $R^a$, $R^c$ and $R^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl TABLE I-1-continued

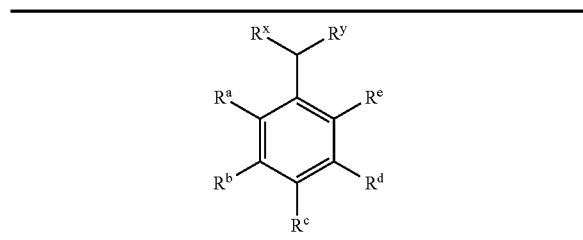

2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^b$ is I; R$^a$, R$^c$ and R$^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl TABLE I-1-continued

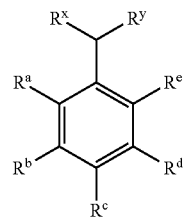

2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl R$^x$ is C(O)OH; R$^y$ is H; R$^a$ and R$^b$ are F; R$^c$ and R$^e$ are H H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl

TABLE I-1-continued

| | |
|---|---|
| 51 | 52 |

2-fluoro-5-chlorophenyl
2,5-dichlorophenyl
2-fluoro-5-(OCF₃)phenyl
2-chloro-5-(CF₃)phenyl
$R^x$ is C(O)OH; $R^y$ is H; $R^a$ is F; $R^b$ is Cl; $R^c$ and $R^e$ are H H
F
Cl
Br
I
cyano
Me
Et
Pr
i-Pr
t-Bu
CF₃
CH₂F
CHF₂
OMe
OEt
O-n-Pr
O-i-Pr
OCF₃
OCHF₂
OCH₂CF₃
SCF₃
SCF₃
SCHF₂
phenyl
2-fluorophenyl
3-chlorophenyl
3-(CF₃)phenyl
3-fluorophenyl
3-cyanophenyl
3-(OCF₃)phenyl
4-fluorophenyl
4-chlorophenyl
4-(CF₃)phenyl
4-cyanophenyl
4-bromophenyl
6-chloro-3-pyridinyl
6-fluoro-3-pyridinyl
6-(CF₃)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF₃)phenyl
2,4-bis(CF₃)phenyl
2-fluoro-4-bromophenyl
2-chloro-4-fluorophenyl
2-(CF₃)-4-fluorophenyl
2-methyl-4-(CF₃)phenyl
2-chloro-4-(CF₃)phenyl
2-(CF₃)-4-chlorophenyl
2,5-difluorophenyl
2-fluoro-5-(CF₃)phenyl
2-fluoro-5-chlorophenyl
2,5-dichlorophenyl 2-fluoro-5-(OCF₃)phenyl
2-chloro-5-(CF₃)phenyl
$R^x$ is C(O)OH; $R^y$ is H; $R^c$ is OMe; $R^a$, $R^b$ and $R^e$ are H H
F
Cl
Br
I
cyano
Me
Et
Pr
i-Pr
t-Bu
CF₃
CH₂F
CHF₂
OMe
OEt
O-n-Pr
O-i-Pr
OCF₃
OCHF₂
OCH₂CF₃
SCF₃
SCF₃
SCHF₂
phenyl
2-fluorophenyl
3-chlorophenyl
3-(CF₃)phenyl
3-fluorophenyl
3-cyanophenyl
3-(OCF₃)phenyl
4-fluorophenyl
4-chlorophenyl
4-(CF₃)phenyl
4-cyanophenyl
4-bromophenyl
6-chloro-3-pyridinyl
6-fluoro-3-pyridinyl
6-(CF₃)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF₃)phenyl
2,4-bis(CF₃)phenyl
2-fluoro-4-bromophenyl
2-chloro-4-fluorophenyl
2-(CF₃)-4-fluorophenyl
2-methyl-4-(CF₃)phenyl
2-chloro-4-(CF₃)phenyl
2-(CF₃)-4-chlorophenyl
2,5-difluorophenyl
2-fluoro-5-(CF₃)phenyl
2-fluoro-5-chlorophenyl
2,5-dichlorophenyl
2-fluoro-5-(OCF₃)phenyl
2-chloro-5-(CF₃)phenyl

TABLE I-1-continued

[Structure: benzene ring with $R^x$, $R^y$ on benzylic carbon; $R^a$, $R^b$, $R^c$, $R^d$, $R^e$ substituents]

$R^x$ is C(O)OH; $R^y$ is H; $R^c$ is Me; $R^a$, $R^b$ and $R^e$ are H

H
F
Cl
Br
I
cyano
Me
Et
Pr
i-Pr
t-Bu
$CF_3$
$CH_2F$
$CHF_2$
OMe
OEt
O-n-Pr
O-i-Pr
$OCF_3$
$OCHF_2$
$OCH_2CF_3$
$SCF_3$
$SCF_3$
$SCHF_2$
phenyl
2-fluorophenyl
3-chlorophenyl
3-($CF_3$)phenyl
3-fluorophenyl
3-cyanophenyl
3-($OCF_3$)phenyl
4-fluorophenyl
4-chlorophenyl
4-($CF_3$)phenyl
4-cyanophenyl
4-bromophenyl
6-chloro-3-pyridinyl
6-fluoro-3-pyridinyl
6-($CF_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-($CF_3$)phenyl
2,4-bis($CF_3$)phenyl
2-fluoro-4-bromophenyl
2-chloro-4-fluorophenyl
2-($CF_3$)-4-fluorophenyl
2-methyl-4-($CF_3$)phenyl
2-chloro-4-($CF_3$)phenyl
2-($CF_3$)-4-chlorophenyl
2,5-difluorophenyl
2-fluoro-5-($CF_3$)phenyl
2-fluoro-5-chlorophenyl
2,5-dichlorophenyl
2-fluoro-5-($OCF_3$)phenyl
2-chloro-5-($CF_3$)phenyl

TABLE I-1-continued

[Structure: benzene ring with $R^x$, $R^y$ on benzylic carbon; $R^a$, $R^b$, $R^c$, $R^d$, $R^e$ substituents]

$R^x$ is C(O)OH; $R^y$ is H; $R^c$ is F; $R^a$, $R^b$ and $R^e$ are H

H
F
Cl
Br
I
cyano
Me
Et
Pr
i-Pr
t-Bu
$CF_3$
$CH_2F$
$CHF_2$
OMe
OEt
O-n-Pr
O-i-Pr
$OCF_3$
$OCHF_2$
$OCH_2CF_3$
$SCF_3$
$SCF_3$
$SCHF_2$
phenyl
2-fluorophenyl
3-chlorophenyl
3-($CF_3$)phenyl
3-fluorophenyl
3-cyanophenyl
3-($OCF_3$)phenyl
4-fluorophenyl
4-chlorophenyl
4-($CF_3$)phenyl
4-cyanophenyl
4-bromophenyl
6-chloro-3-pyridinyl
6-fluoro-3-pyridinyl
6-($CF_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-($CF_3$)phenyl
2,4-bis($CF_3$)phenyl
2-fluoro-4-bromophenyl
2-chloro-4-fluorophenyl
2-($CF_3$)-4-fluorophenyl
2-methyl-4-($CF_3$)phenyl
2-chloro-4-($CF_3$)phenyl
2-($CF_3$)-4-chlorophenyl
2,5-difluorophenyl
2-fluoro-5-($CF_3$)phenyl
2-fluoro-5-chlorophenyl
2,5-dichlorophenyl
2-fluoro-5-($OCF_3$)phenyl
2-chloro-5-($CF_3$)phenyl TABLE I-1-continued

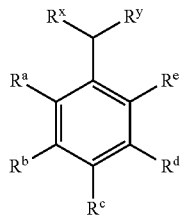

$R^x$ is C(O)OH; $R^y$ is H; $R^c$ is Cl; $R^a$, $R^b$ and $R^e$ are H

H
F
Cl
Br
I
cyano
Me
Et
Pr
i-Pr
t-Bu
CF$_3$
CH$_2$F
CHF$_2$
OMe
OEt
O-n-Pr
O-i-Pr
OCF$_3$
OCHF$_2$
OCH$_2$CF$_3$
SCF$_3$
SCF$_3$
SCHF$_2$
phenyl
2-fluorophenyl
3-chlorophenyl
3-(CF$_3$)phenyl
3-fluorophenyl
3-cyanophenyl
3-(OCF$_3$)phenyl
4-fluorophenyl
4-chlorophenyl
4-(CF$_3$)phenyl
4-cyanophenyl
4-bromophenyl
6-chloro-3-pyridinyl
6-fluoro-3-pyridinyl
6-(CF$_3$)-3-pyridinyl
4,6-dichloro-3-pyridinyl
2-fluoro-6-chloro-3-pyridinyl
2,6-dichloro-3-pyridinyl
2-bromo-5-chloro-4-pyridinyl
3-bromo-5-fluorophenyl
3-chloro-5-fluorophenyl
3-fluoro-4-chlorophenyl
2,4-dichlorophenyl
2,4-difluorophenyl
2-fluoro-4-cyanophenyl
2-fluoro-4-chlorophenyl
2-methyl-4-chlorophenyl
2-fluoro-4-(CF$_3$)phenyl
2,4-bis(CF$_3$)phenyl
2-fluoro-4-bromophenyl
2-chloro-4-fluorophenyl
2-(CF$_3$)-4-fluorophenyl
2-methyl-4-(CF$_3$)phenyl
2-chloro-4-(CF$_3$)phenyl
2-(CF$_3$)-4-chlorophenyl
2,5-difluorophenyl
2-fluoro-5-(CF$_3$)phenyl
2-fluoro-5-chlorophenyl
2,5-dichlorophenyl
2-fluoro-5-(OCF$_3$)phenyl
2-chloro-5-(CF$_3$)phenyl TABLE I-1-continued

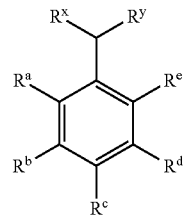

$R^x$ is C(O)OH; $R^y$ is H; $R^a$ and $R^e$ are F; $R^c$ and $R^d$ are H

| $R^b$ |
| --- |
| H |
| F |
| Cl |
| Br |
| I |
| cyano |
| Me |
| Et |
| Pr |
| i-Pr |
| t-Bu |
| CF$_3$ |
| CH$_2$F |
| CHF$_2$ |
| OMe |
| OEt |
| O-n-Pr |
| O-i-Pr |
| OCF$_3$ |
| OCHF$_2$ |
| OCH$_2$CF$_3$ |
| SCF$_3$ |
| SCF$_3$ |
| SCHF$_2$ |
| phenyl |
| 2-fluorophenyl |
| 3-chlorophenyl |
| 3-(CF$_3$)phenyl |
| 3-fluorophenyl |
| 3-cyanophenyl |
| 3-(OCF$_3$)phenyl |
| 4-fluorophenyl |
| 4-chlorophenyl |
| 4-(CF$_3$)phenyl |
| 4-cyanophenyl |
| 4-bromophenyl |
| 6-chloro-3-pyridinyl |
| 6-fluoro-3-pyridinyl |
| 6-(CF$_3$)-3-pyridinyl |
| 4,6-dichloro-3-pyridinyl |
| 2-fluoro-6-chloro-3-pyridinyl |
| 2,6-dichloro-3-pyridinyl |
| 2-bromo-5-chloro-4-pyridinyl |
| 3-bromo-5-fluorophenyl |
| 3-chloro-5-fluorophenyl |
| 3-fluoro-4-chlorophenyl |
| 2,4-dichlorophenyl |
| 2,4-difluorophenyl |
| 2-fluoro-4-cyanophenyl |
| 2-fluoro-4-chlorophenyl |
| 2-methyl-4-chlorophenyl |
| 2-fluoro-4-(CF$_3$)phenyl |
| 2,4-bis(CF$_3$)phenyl |
| 2-fluoro-4-bromophenyl |
| 2-chloro-4-fluorophenyl |
| 2-(CF$_3$)-4-fluorophenyl |
| 2-methyl-4-(CF$_3$)phenyl |
| 2-chloro-4-(CF$_3$)phenyl |
| 2-(CF$_3$)-4-chlorophenyl |
| 2,5-difluorophenyl |
| 2-fluoro-5-(CF$_3$)phenyl |
| 2-fluoro-5-chlorophenyl |
| 2,5-dichlorophenyl |

TABLE I-1-continued

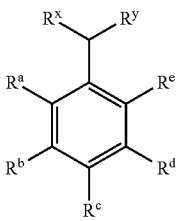

2-fluoro-5-(OCF$_3$)phenyl
2-chloro-5-(CF$_3$)phenyl

Table I-2

Table I-2 is identical to Table I-1, except that R$^x$ is C(O)OMe.

Table I-3

Table I-3 is identical to Table I-1, except that R$^x$ is C(O)OEt.

Table I-4

Table I-4 is identical to Table I-1, except that R$^x$ is C(O)OPh.

Table I-5

Table I-5 is identical to Table I-1, except that R$^x$ is C(O)OC(CH$_3$)$_3$.

Table I-6

Table I-6 is identical to Table I-1, except that R$^x$ is C(O)O(2,4,6-trichlorophenyl).

Table I-7

Table I-7 is identical to Table I-1, except that R$^x$ is C(O)O(4-nitrophenyl).

Table I-8

Table I-8 is identical to Table I-1, except that R$^x$ is C(O)OH and R$^y$ is C(O)OH.

Table I-9

Table I-9 identical to Table I-1, except that R$^x$ is C(O)OH and R$^y$ is C(O)OMe.

Table I-10

Table I-10 is constructed the same as Table I-1, except that R$^x$ is C(O)OH and R$^y$ is C(O)OEt.

Table I-11

Table I-11 identical to Table I-1, except that R$^x$ is C(O)OH and R$^y$ is C(O)OC(CH$_3$)$_3$.

Table I-12

Table I-12 identical to Table I-1, except that R$^x$ is C(O)OH and R$^y$ is C(O)OPh.

Table I-13

Table I-13 identical to Table I-1, except that R$^x$ is C(O)OH and R$^y$ is C(O)O(2,4,6-trichlorophenyl).

Table I-14

Table I-14 identical to Table I-1, except that R$^x$ is C(O)OH and R$^y$ is C(O)O(4-nitrophenyl).

Table I-15

Table I-15 is identical to Table I-1, except that R$^x$ is C(O)OPh and R$^y$ is C(O)OMe.

Table I-16

Table I-16 is identical to Table I-1, except that R$^x$ is C(O)OPh and R$^y$ is C(O)OEt.

Table I-17

Table I-17 is identical to Table I-1, except that R$^x$ is C(O)OPh and R$^y$ is C(O)OC(CH$_3$)$_3$.

Table I-18

Table I-18 is identical to Table I-1, except that R$^x$ is C(O)OPh and R$^y$ is C(O)OPh.

Table I-19

Table I-19 is identical to Table I-1, except that R$^x$ is C(O)OPh and R$^y$ is C(O)0(2,4,6-trichlorophenyl).

Table I-20

Table I-20 is identical to Table I-1, except that R$^x$ is C(O)OPh and R$^y$ is C(O)O(4-nitrophenyl).

Table I-21

Table I-21 is identical to Table I-1, except that R$^x$ is C(O)Cl and R$^y$ is C(O)Cl.

Table I-22

Table I-22 is identical to Table I-1, except that R$^x$ is C(O)OMe and R$^y$ is C(O)OMe.

Table I-23

Table I-23 is identical to Table I-1, except that R$^x$ is C(O)OEt and R$^y$ is C(O)OEt.

Table I-24

Table I-24 is identical to Table I-1, except that R$^x$ is C(O)OC(CH$_3$)$_3$ and R$^y$ is C(O)OC(CH$_3$)$_3$.

Table I-25

Table I-25 is identical to Table I-1, except that R$^x$ is C(O)O(2,4,6-trichlorophenyl) and R$^y$ is C(O)O(2,4,6-trichlorophenyl).

Table I-26

Table I-26 is identical to Table I-1, except that $R^x$ is C(O)O(4-nitrophenyl) and $R^y$ is C(O)O(4-nitrophenyl).

Table I-27

Table I-27 is identical to Table I-1, except that $R^x$ is C(O)(3-methyl-2-pyridinylamino) and $R^y$ is C(O)OH.

Table I-28

Table I-28 is identical to Table I-1, except that $R^x$ is C(O)(3-methyl-2-pyridinylamino) and $R^y$ is C(O)OMe.

Table I-29

Table I-29 is identical to Table I-1, except that $R^x$ is C(O)(3-methyl-2-pyridinylamino) and $R^y$ is C(O)OEt.

Table I-30

Table I-30 is identical to Table I-1, except that $R^x$ is C(O)(3-methyl-2-pyridinylamino) and $R^y$ is C(O)OPh.

Table I-31

Table I-31 is identical to Table I-1, except that $R^x$ is C(O)(3-methyl-2-pyridinylamino) and $R^y$ is C(O)O(2,4,6-trichlorophenyl).

Table I-32

Table I-32 is identical to Table I-1, except that $R^x$ is C(O)(3-methyl-2-pyridinylamino) and $R^y$ is C(O)O(4-nitrophenyl).

Table I-33

Table I-33 is identical to Table I-1, except that $R^x$ is C(O)(3-methyl-2-pyridinylamino) and $R^y$ is C(O)OC(CH$_3$)$_3$.

Table I-34

Table I-34 is identical to Table I-1, except that the chemical structure under the Table I-1 heading is replaced with the following structure, and R is Cl. The groups $R^x$ and $R^y$ found in Table I-1 are not relevant to Table I-34, as the CH($R^x$)($R^y$) moiety in the structure of Table I-1 is replaced with a R group in the structure of Table I-34.

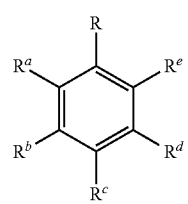

For example, the first compound in Table I-34 is the structure shown immediately above wherein $R^a$, $R^b$, $R^c$, $R^d$ and $R^e$ are H, and R is Cl.

Table I-35

Table I-35 is identical to Table I-34, except that R is Br.

Table I-36

Table I-36 is identical to Table I-34, except that R is I.

Table I-37

Table I-37 is identical to Table I-34, except that R is CH$_2$OH.

Table I-38

Table I-38 is identical to Table I-34, except that R is CH$_2$CN.

Table I-39

Table I-39 is identical to Table I-34, except that R is CH$_2$Cl.

Table I-40

Table I-40 is identical to Table I-34, except that R is CH(CN)CO$_2$Me.

Table I-41

Table I-41 is identical to Table I-34, except that R is CH(CN)CO$_2$Et.

TABLE 1-42

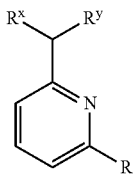

| $R^x$ | $R^y$ |
|---|---|
| R is CF$_3$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is H | |

TABLE 1-42-continued

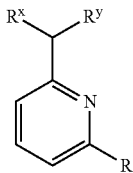

| Rˣ | Rʸ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |
| R is Cl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

TABLE 1-42-continued

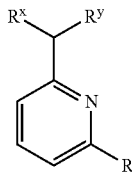

| Rˣ | Rʸ |
|---|---|
| R is Br | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |
| R is I | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |

TABLE 1-42-continued

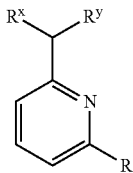

| R$^x$ | R$^y$ |
|---|---|
| H | C(O)OPh |
| H | C(O)OC(CH$_3$)$_3$ |
| R is NH$_2$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-chloro-4-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |

TABLE 1-42-continued

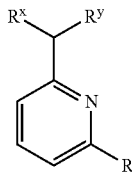

| R$^x$ | R$^y$ |
|---|---|
| H | C(O)OEt |
| H | C(O)OPh |
| H | C(O)OC(CH$_3$)$_3$ |
| R is 2-fluoro-5-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-chloro-4-cyanophenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |

TABLE 1-42-continued

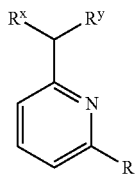

| $R^x$ | $R^y$ |
|---|---|
| H | C(O)OMe |
| H | C(O)OEt |
| H | C(O)OPh |
| H | C(O)OC(CH$_3$)$_3$ |

R is 2-fluoro-4-cyanophenyl

| $R^x$ | $R^y$ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

TABLE 1-43

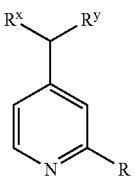

| $R^x$ | $R^y$ |
|---|---|

R is H

| $R^x$ | $R^y$ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |

TABLE 1-43-continued

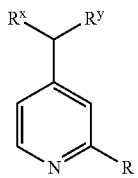

| $R^x$ | $R^y$ |
|---|---|
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is CF$_3$

| $R^x$ | $R^y$ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is F

| $R^x$ | $R^y$ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |

TABLE 1-43-continued

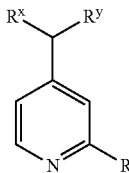

| $R^x$ | $R^y$ |
|---|---|
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is Cl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is Br | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |

TABLE 1-43-continued

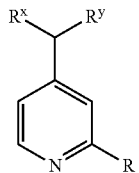

| $R^x$ | $R^y$ |
|---|---|
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is I | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is NH$_2$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |

TABLE 1-43-continued

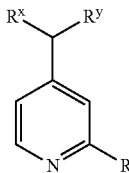

| $R^x$ | $R^y$ |
|---|---|
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is 2-chloro-4-(trifluoromethyl)phenyl

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is 2-fluoro-5-(trifluoromethyl)phenyl

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |

TABLE 1-43-continued

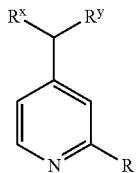

| $R^x$ | $R^y$ |
|---|---|
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is 2-chloro-4-cyanophenyl

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

R is 2-fluoro-4-cyanophenyl

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |

TABLE 1-43-continued

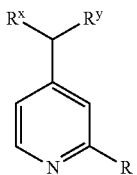

| $R^x$ | $R^y$ |
|---|---|
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. Compound numbers refer to compounds in Index Table A.

SYNTHESIS EXAMPLE 1

Preparation of 2-hydroxy-4-oxo-1-(5-pyrimidinylmethyl)-3-[3-(trifluoromethyl)phenyl]-4H-pyrido[1,2-a]pyrimidinium inner salt (compound 3)

Step A: Preparation of N-(5-pyrimidinylmethylene)-2-pyridinamine

A solution of 2-aminopyridine (11.314 g, 120.3 mmole) and pyrimidine-5-carboxaldehyde (14.0 g, 129.6 mmole) in chloroform (300 mL) was stirred at room temperature for 15 minutes. The volatiles were then removed under reduced pressure (1 hour at 75° C.) to yield a yellow solid. The crude solid was dissolved in chloroform (300 mL), and the solution was stirred for 15 minutes. The volatiles were then removed under reduced pressure (1 hour at 75° C.) to yield a yellow solid. The crude solid was again dissolved in chloroform (300 mL), the solution was stirred for 15 minutes, and the volatiles were removed under reduced pressure (1 hour at 85° C.) to yield a yellow solid. This solid was dried in a vacuum oven overnight at 80° C. to yield 22.090 g (99.8%) of the title compound. $^1$H NMR (CDCl$_3$) δ 9.26-9.32 (m, 4H), 8.52 (d, 1H), 7.82 (t, 1H), 7.42 (d, 1H), 7.26 (t, 1H).

Step B: Preparation of N-[(5-pyrimidinyl)methyl]-2-pyridinamine

Powdered 98% sodium borohydride (2.868 g, 75.5 mmole) was added to solution of methanol (80 mL) and tetrahydrofuran (400 mL), and the mixture was stirred vigorously for 5 minutes. The product of Step A (13.9 g, 75.5 mmole) was dissolved in tetrahydrofuran (400 mL), and the resulting solution was added dropwise to the sodium borohydride suspension at a constant rate of approximately 33 mL/minute. The appearance of the reaction mixture changed from a light yellow slightly cloudy suspension to a clear red solution. Reaction progress was monitored by thin layer chromatography eluting with a 10% methanol: 40% dichloromethane: 50% toluene solvent. Upon reaction completion, acetic acid (3 mL) was added dropwise, and the reaction mixture was stirred for 5 minutes. Acetic acid (2 mL) and water (30 mL) were added, the reaction mixture was briefly stirred, and then ethyl acetate was added (500 mL). The reaction mixture was washed with 1N aqueous sodium hydroxide solution (300 mL), dried over magnesium sulfate, filtered, and the solvent was removed under reduced pressure at 50° C. The resulting crude oil was dissolved in dichloromethane (50 mL), and the solution was eluted through a plug of silica gel (100 g) with ethyl acetate (3 L). The eluant was concentrated to a yellow-orange oil which slowly crystallized to provide 8.909 g (63.4%) of the title product as a pale yellow solid. $^1$H NMR (CDCl$_3$) δ 9.12 (s, 1H), 8.76 (s, 2H), 8.10 (d, 1H), 7.42 (t, 1H), 6.64 (t, 1H), 6.42 (d, 1H), 4.99 (br s, NH), 4.61 (d, 2H).

Step C: Preparation of 1,3-dimethyl 2-[3-(trifluoromethyl)phenyl]propanedioate

Dioxane (100 mL) was purged with nitrogen gas for 10 minutes. Phenanthrolene (1.0 g) and copper (I) iodide (1.0 g) were added to the dioxane, the suspension was allowed to stir under a nitrogen atmosphere for 5 minutes, and then cesium carbonate (18.72 g, 57.45 mmol), dimethyl malonate (5.46 g, 50.6 mmol), and 1-iodo-3-(trifluoromethyl)benzene (12.5 g, 46.0 mmol) were added. The reaction mixture was heated to reflux for 18 hours and then cooled to room temperature. Aqueous 1N HCl was added to the reaction mixture, the layers were separated, and the aqueous layer was extracted with ethyl acetate (3×100 mL). The combined organic layers were dried over magnesium sulfate and filtered. Celite® diatomaceous filter aid (5 g) was added to the filtrate, and the resulting suspension was concentrated under reduced pressure at 50° C. to yield a solid consisting of the crude product adsorbed onto Celite®. This solid was purified by silica gel chromatography eluting with a gradient of 100% hexanes to 25% ethyl acetate in hexanes to yield 7.36 g (58.0%) of the title product. $^1$H NMR (CDCl$_3$) δ 7.59-7.65 (m, 3H), 7.49 (t, 1H), 4.70 (s, 1H), 3.76 (s, 6H).

Step D: Preparation of bis(2,4,6-trichlorophenyl) 2-[3-(trifluoromethyl)phenyl]propanedioate The product of Step C was added to a solution of NaOH (25 g) in water (75 mL), and the reaction mixture was vigorously stirred under a nitrogen atmosphere at 60° C. for 8 minutes. The reaction mixture was then added to ice (100 g), and aqueous 6 N HCl was added until a pH of 1 was reached. The solution was extracted with ethyl acetate (3×100 mL), and the combined organic extracts were dried over magnesium sulfate, filtered, and concentrated under reduced pressure. Dichloromethane (200 mL) was added to the resulting white solid, followed by the addition of oxalyl chloride (5 mL) and N,N-dimethylformamide (0.5 mL). The reaction mixture was stirred at room temperature for 2 hours, followed by the addition of 2,4,6-trichlorophenol (10.528 g, 53.32 mmol). After stirring overnight at room temperature, the reaction mixture was concentrated under reduced pressure. Methanol was added to the resulting residue, and a solid slowly precipitated from the solution. The solid was collected by filtration to provide 8.161 g (50.43%) of the title product as a solid. $^1$H NMR (CDCl$_3$) δ 7.91 (s, 1H), 7.83 (d, 1H), 7.70 (d, 1H), 7.59 (t, 1H), 7.37 (s, 4H), 5.38 (s, 1H).

Step E: Preparation of 2-hydroxy-4-oxo-1-(5-pyrimidinylmethyl)-3-[3-(trifluoromethyl)phenyl]-4H-pyrido[1,2-c]pyrimidinium inner salt To the product of Step D (8.16 g, 13.4 mmol) in toluene (100 mL) was added the product of Step B (3.31 g, 17.8 mmol). The reaction mixture was heated to 110° C. for 6 hours, during which time a yellow solid precipitated out of solution. The reaction mixture was concentrated in the presence of Celite®, and the crude product adsorbed onto Celite® was purified by silica gel chromatography eluting with a gradient of 100% ethyl acetate to 25% methanol in ethyl acetate to yield 7.36 g (58.0%) of the title product, a compound of this invention.

Synthesis Example 2

Preparation of 3-(4'-cyano-5,2'-dimethyl[1,1'-biphenyl]-3-yl)-2-hydroxy-4-oxo-1-(5-pyrimidinylmethyl)-4H-pyrido[1,2-c]pyrimidinium inner salt (compound 18)

Step A: Preparation of 1,3-bis(1,1-dimethylethyl) 2-(3-iodo-5-methylphenyl)propanedioate Copper iodide (332 mg, 1.74 mmol), cesium carbonate (5.6 g, 17.4 mmol), and picolinic acid (429 mg, 3.49 mmol) were added to a dried flask under a nitrogen atmosphere. A solution of 3,5-diiodotoluene (3 g, 8.7 mmol) in dioxane (10 mL) was added, followed by the addition of di-tert-butyl malonate (1.3 mL, 8.7 mmol). The atmosphere inside the flask was removed under vacuum and replaced with nitrogen gas; this process was repeated a total of three times. The reaction mixture was then heated to 80° C. and stirred for 24 hours. The reaction mixture was then cooled to room temperature, quenched with saturated aqueous ammonium chloride solution (50 mL), and extracted twice with diethyl ether (50 mL). The organic layers were combined, dried over MgSO$_4$, and concentrated under reduced pressure. The resulting residue was purified by chromatography on silica gel eluted with ethyl acetate in hexanes to provide the title product as an orange oil (0.62 g).
$^1$H NMR (CDCl$_3$) δ 7.50 (dd 2H), 7.15 (s, 1H), 4.30 (s, 1H), 2.30 (s, 3H), 1.47 (m, 18H).

Step B: Preparation 1,3-bis(1,1-dimethylethyl) 2-(4'-cyano-5,2'-dimethyl[1,1'-biphenyl]-3-yl)propanedioate A mixture of 1,3-bis(1,1-dimethylethyl) 2-(3-iodo-5-methylphenyl)propanedioate (the product of Step A, 320 mg, 0.74 mmol), 4-cyano-2-methylphenylboronic acid (178 mg, 1.11 mmol), sodium carbonate (78 mg, 0.74 mmol), bis(triphenylphosphine)palladium(II) dichloride (52 mg, 0.074 mmol), dioxane (5 mL), and water (1 mL) was heated to 80° C. and stirred for 20 minutes. The reaction mixture was then cooled to room temperature, and filtered through a plug of silica gel eluting with 20% ethyl acetate in hexanes. Concentration of the eluant under reduced pressure provided a brown oil (430 mg) containing the crude product, which was used in the next step without further purification.
$^1$H NMR (CDCl$_3$) δ 7.70-7.10 (m, 6H), 4.436 (s, 1H), 2.402 (s, 3H), 2.289 (s, 3H), 1.469 (s, 18H).

Step C: Preparation of 3-(4'-cyano-5,2'-dimethyl[1,1'-biphenyl]-3-yl)-2-hydroxy-4-oxo-1-(5-pyrimidinylmethyl)-4H-pyrido[1,2-a]pyrimidinium inner salt A mixture of N-[(5-pyrimidinyl)methyl]-2-pyridinamine (65 mg, 0.34 mmol) and 1,3-bis(1,1-dimethylethyl) 2-(4'-cyano-5,2'-dimethyl[1,1'-biphenyl]-3-yl)propanedioate (the product of Step B, 120 mg, 0.28 mmol) in p-cymene (2 mL) and 1,2,3,4-tetrahydronaphthalene (i.e. tetralin, 1 mL) was heated to 178° C. and stirred for 1.5 hours. The reaction mixture was then cooled to room temperature, and purified by chromatography on silica gel eluted with 20% methanol in ethyl acetate to provide 40 mg (25%) of the title compound, a compound of this invention, as a yellow solid.
$^1$H NMR ((CD$_3$)$_2$CO) δ 9.5 (dd, 1H), 9.05 (s, 1H), 8.95 (d, 2H), 8.35 (m, 1H), 7.95 (dd, 1H), 7.80 (d, 1H), 7.75 (s, 1H), 7.70 (s, 1H), 7.65 (m, 1H), 7.55 (m, 1H), 7.45 (dd, 1H), 7.0 (d, 1H), 5.75 (s, 2H), 2.06 (d, 6H).

By the procedures described herein together with methods known in the art, the following compounds of Tables 1 and 2 can be prepared. The following abbreviations are used in Table 1: Me means methyl, Et means ethyl, Pr means propyl and Bu means butyl.

TABLE 1

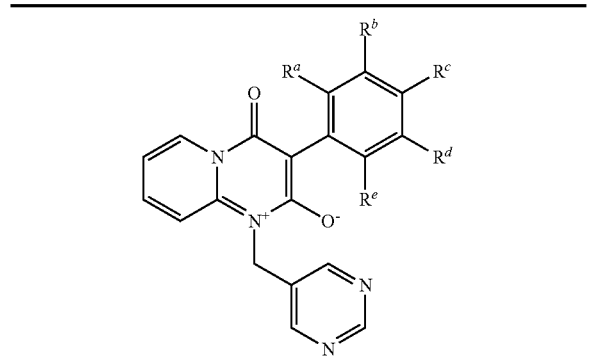

$R^b$, $R^c$, $R^d$ and $R^e$ are H

| $R^a$ | $R^a$ | $R^a$ | $R^a$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$, $R^c$, $R^d$ and $R^e$ are H

| $R^b$ | $R^b$ | $R^b$ | $R^b$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued $R^a$, $R^b$, $R^d$ and $R^e$ are H

| $R^c$ | $R^c$ | $R^c$ | $R^c$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is F; $R^c$, $R^d$ and $R^e$ are H

| $R^b$ | $R^b$ | $R^b$ | $R^b$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

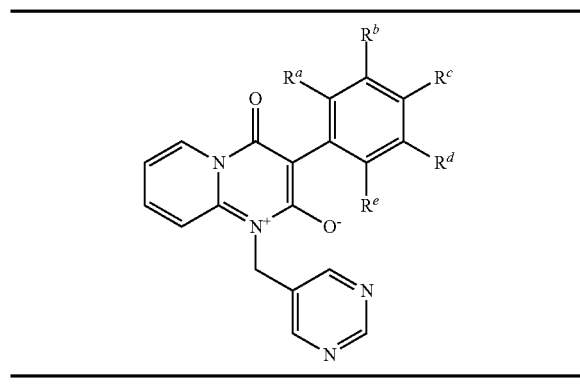

| | | | |
|---|---|---|---|
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is F; $R^b$, $R^d$ and $R^e$ are H

| $R^c$ | $R^c$ | $R^c$ | $R^c$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is F; $R^b$, $R^c$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

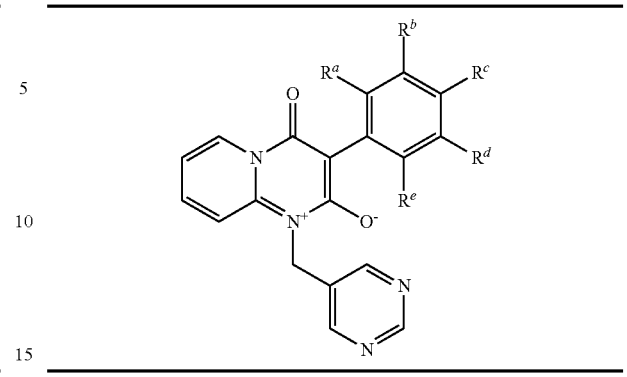

| | | | |
|---|---|---|---|
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is F; $R^b$, $R^c$ and $R^d$ are H

| $R^e$ | $R^e$ | $R^e$ | $R^e$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is Cl; $R^c$, $R^d$ and $R^e$ are H

| $R^b$ | $R^b$ | $R^b$ | $R^b$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

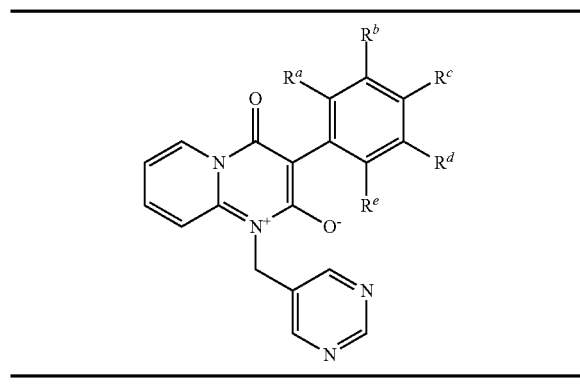

| $R^c$ | $R^c$ | $R^c$ | $R^c$ |
|---|---|---|---|
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

$R^a$ is Cl; $R^b$, $R^d$ and $R^e$ are H

| $R^c$ | $R^c$ | $R^c$ | $R^c$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

$R^a$ is Cl; $R^b$, $R^c$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

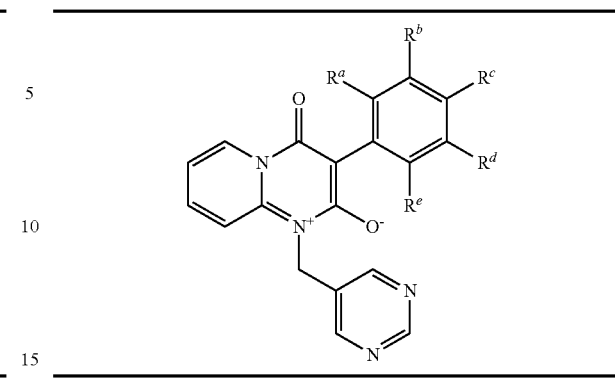

| $R^e$ | $R^e$ | $R^e$ | $R^e$ |
|---|---|---|---|
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

$R^a$ is Cl; $R^b$, $R^c$ and $R^d$ are H

| $R^e$ | $R^e$ | $R^e$ | $R^e$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

$R^a$ is OMe; $R^c$, $R^d$ and $R^e$ are H

| $R^b$ | $R^b$ | $R^b$ | $R^b$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

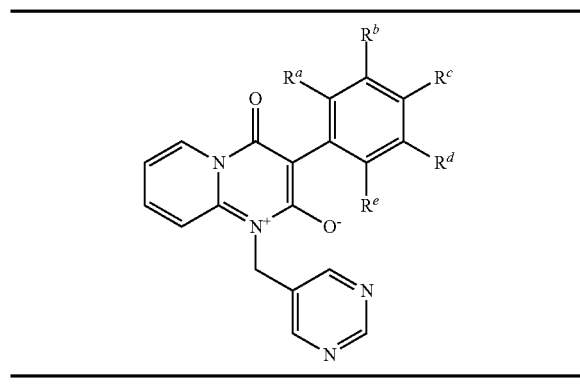

| | | | |
|---|---|---|---|
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^a$ is OMe; $R^b$, $R^d$ and $R^e$ are H

| $R^c$ | $R^c$ | $R^c$ | $R^c$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^a$ is OMe; $R^b$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |

TABLE 1-continued

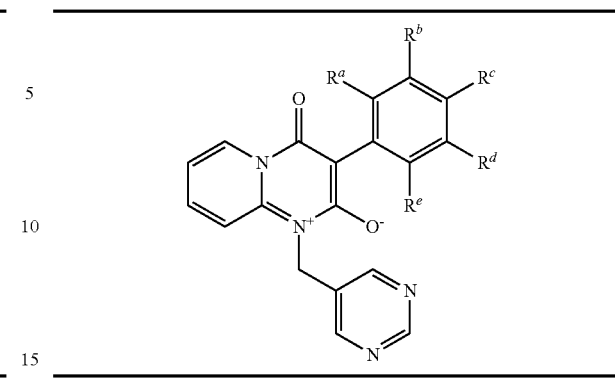

| | | | |
|---|---|---|---|
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^a$ is OMe; $R^b$, $R^c$ and $R^d$ are H

| $R^e$ | $R^e$ | $R^e$ | $R^e$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^a$ is Me; $R^c$, $R^d$ and $R^e$ are H

| $R^b$ | $R^b$ | $R^b$ | $R^b$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |

TABLE 1-continued

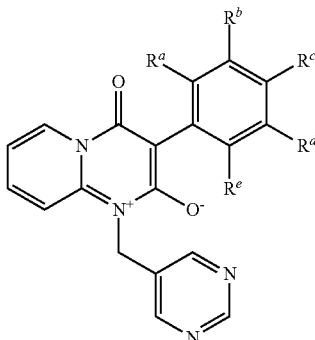

| $R^a$ is Me; $R^b$, $R^d$ and $R^e$ are H | | | |
|---|---|---|---|
| $R^c$ | $R^c$ | $R^c$ | $R^c$ |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

| $R^a$ is Me; $R^b$, $R^d$ and $R^e$ are H | | | |
|---|---|---|---|
| $R^c$ | $R^c$ | $R^c$ | $R^c$ |
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

| $R^a$ is Me; $R^b$, $R^c$ and $R^e$ are H | | | |
|---|---|---|---|
| $R^d$ | $R^d$ | $R^d$ | $R^d$ |
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

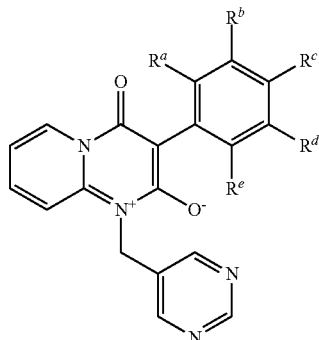

| $R^a$ is Me; $R^b$, $R^c$ and $R^d$ are H | | | |
|---|---|---|---|
| $R^e$ | $R^e$ | $R^e$ | $R^e$ |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

| $R^a$ is Me; $R^b$, $R^c$ and $R^d$ are H | | | |
|---|---|---|---|
| $R^e$ | $R^e$ | $R^e$ | $R^e$ |
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF$_3$)phenyl | 2-methyl-4-chlorophenyl | |

| $R^d$ is Cl; $R^a$, $R^c$ and $R^e$ are H | | | |
|---|---|---|---|
| $R^b$ | $R^b$ | $R^b$ | $R^b$ |
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluorophenyl | 3-fluoro-4-chlorophenyl | 2,5-dichlorophenyl |
| CHF$_2$ | 3-cyanophenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |

TABLE 1-continued

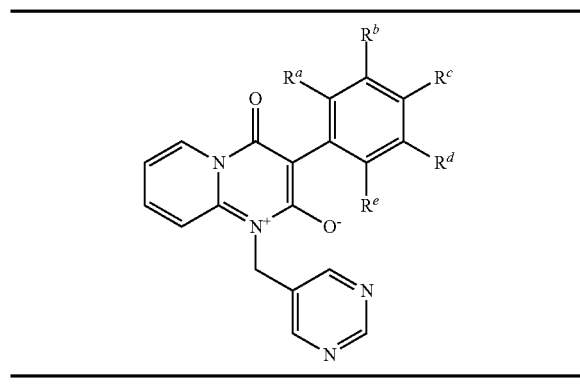

| | | | |
|---|---|---|---|
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF₃)phenyl | 2-methyl-4-chlorophenyl | |

$R^d$ is CF₃; $R^a$, $R^c$ and $R^e$ are H

| $R^b$ | $R^b$ | $R^b$ | $R^b$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluoro-phenyl | 3-fluoro-4-chlorophenyl | 2,5-dichlorophenyl |
| CHF₂ | 3-cyano-phenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF₃)phenyl | 2-methyl-4-chlorophenyl | |

$R^b$ is Br; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluoro-phenyl | 3-fluoro-4-chlorophenyl | 2,5-dichlorophenyl |
| CHF₂ | 3-cyano-phenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |

TABLE 1-continued

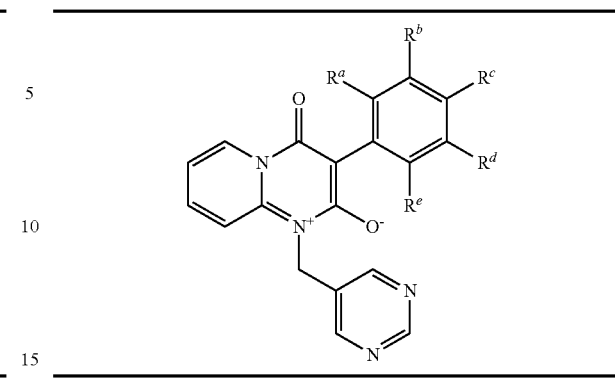

| | | | |
|---|---|---|---|
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF₃)phenyl | 2-methyl-4-chlorophenyl | |

$R^b$ is OCF₃; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluoro-phenyl | 3-fluoro-4-chlorophenyl | 2,5-dichlorophenyl |
| CHF₂ | 3-cyano-phenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF₃)phenyl | 2-methyl-4-chlorophenyl | |

$R^b$ is OMe; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluoro-phenyl | 3-fluoro-4-chlorophenyl | 2,5-dichlorophenyl |
| CHF₂ | 3-cyano-phenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluoro-phenyl | 2-fluoro-4-cyanophenyl | |

TABLE 1-continued

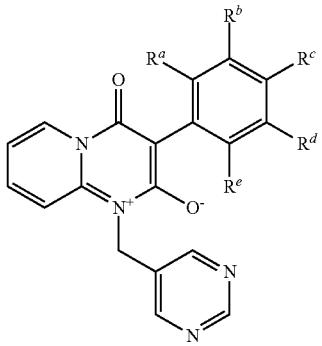

O-n-Pr  4-chlorophenyl  2-fluoro-4-chlorophenyl
O-i-Pr  4-(CF₃)phenyl  2-methyl-4-chlorophenyl $R^b$ is F; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^b$ is CN; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |

TABLE 1-continued

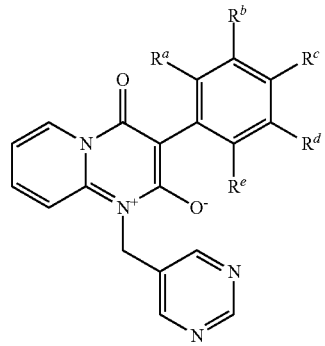

O-n-Pr  4-chlorophenyl  2-fluoro-4-chlorophenyl
O-i-Pr  4-(CF₃)phenyl  2-methyl-4-chlorophenyl $R^b$ is Me; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |
| O-n-Pr | 4-chlorophenyl | 2-fluoro-4-chlorophenyl | |
| O-i-Pr | 4-(CF₃)phenyl | 2-methyl-4-chlorophenyl | |

$R^b$ is I; $R^a$, $R^c$ and $R^e$ are H

| $R^d$ | $R^d$ | $R^d$ | $R^d$ |
|---|---|---|---|
| H | OCF₃ | 4-cyanophenyl | 2-fluoro-4-(CF₃)phenyl |
| F | OCHF₂ | 4-bromophenyl | 2,4-bis(CF₃)phenyl |
| Cl | OCH₂CF₃ | 6-chloro-3-pyridinyl | 2-fluoro-4-bromophenyl |
| Br | SCF₃ | 6-fluoro-3-pyridinyl | 2-chloro-4-fluorophenyl |
| I | SCF₃ | 6-(CF₃)-3-pyridinyl | 2-(CF₃)-4-fluorophenyl |
| Me | SCHF₂ | 4,6-dichloro-3-pyridinyl | 2-methyl-4-(CF₃)phenyl |
| Et | cyano | 2-fluoro-6-chloro-3-pyridinyl | 2-chloro-4-(CF₃)phenyl |
| Pr | phenyl | 2,6-dichloro-3-pyridinyl | 2-(CF₃)-4-chlorophenyl |
| i-Pr | 2-fluorophenyl | 2-bromo-5-chloro-4-pyridinyl | 2,5-difluorophenyl |
| t-Bu | 3-chlorophenyl | 3-bromo-5-fluorophenyl | 2-fluoro-5-(CF₃)phenyl |
| CF₃ | 3-(CF₃)phenyl | 3-chloro-5-fluorophenyl | 2-fluoro-5-chlorophenyl |
| CH₂F | 3-fluorophenyl | 3-fluoro-4-chlorophenyl | 2,5-dichlorophenyl |
| CHF₂ | 3-cyanophenyl | 2,4-dichlorophenyl | 2-fluoro-5-(OCF₃)phenyl |
| OMe | 3-(OCF₃)phenyl | 2,4-difluorophenyl | 2-chloro-5-(CF₃)phenyl |
| OEt | 4-fluorophenyl | 2-fluoro-4-cyanophenyl | |

TABLE 1-continued

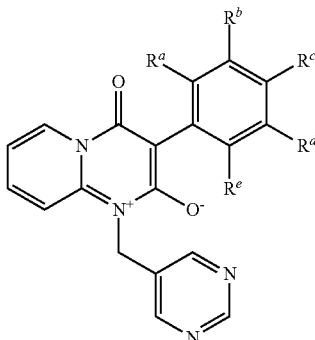

| | | | |
|---|---|---|---|
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ and $R^b$ are F; $R^c$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ is F; $R^b$ is Cl; $R^c$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |

TABLE 1-continued

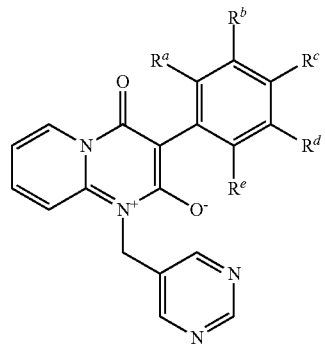

| | | | |
|---|---|---|---|
| O-n-Pr | 4-chloro-phenyl | 2-fluoro-4-chlorophenyl | |
| O-i-Pr | 4-(CF$_3$)phenyl | 2-methyl-4-chlorophenyl | |

$R^c$ is OMe; $R^a$, $R^b$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^c$ is Me; $R^a$, $R^b$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |

TABLE 1-continued

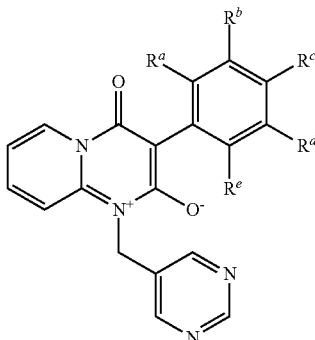

| | | | |
|---|---|---|---|
| O-n-Pr | 4-chloro-phenyl | 2-fluoro-4-chlorophenyl | |
| O-i-Pr | 4-(CF$_3$)phenyl | 2-methyl-4-chlorophenyl | |

$R^c$ is F; $R^a$, $R^b$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

$R^c$ is Cl; $R^a$, $R^b$ and $R^e$ are H

| $R^d$ | $R^d$ | $R^d$ | $R^d$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |

TABLE 1-continued

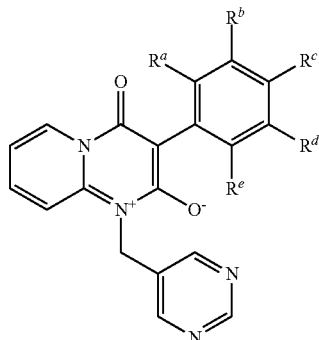

| | | | |
|---|---|---|---|
| O-n-Pr | 4-chloro-phenyl | 2-fluoro-4-chlorophenyl | |
| O-i-Pr | 4-(CF$_3$)phenyl | 2-methyl-4-chlorophenyl | |

$R^a$ and $R^e$ are F; $R^c$ and $R^d$ are H

| $R^b$ | $R^b$ | $R^b$ | $R^b$ |
|---|---|---|---|
| H | OCF$_3$ | 4-cyanophenyl | 2-fluoro-4-(CF$_3$)phenyl |
| F | OCHF$_2$ | 4-bromophenyl | 2,4-bis(CF$_3$)phenyl |
| Cl | OCH$_2$CF$_3$ | 6-chloro-3-pyridinyl | 2-fluoro-4-bromophenyl |
| Br | SCF$_3$ | 6-fluoro-3-pyridinyl | 2-chloro-4-fluorophenyl |
| I | SCF$_3$ | 6-(CF$_3$)-3-pyridinyl | 2-(CF$_3$)-4-fluorophenyl |
| Me | SCHF$_2$ | 4,6-dichloro-3-pyridinyl | 2-methyl-4-(CF$_3$)phenyl |
| Et | cyano | 2-fluoro-6-chloro-3-pyridinyl | 2-chloro-4-(CF$_3$)phenyl |
| Pr | phenyl | 2,6-dichloro-3-pyridinyl | 2-(CF$_3$)-4-chlorophenyl |
| i-Pr | 2-fluoro-phenyl | 2-bromo-5-chloro-4-pyridinyl | 2,5-difluorophenyl |
| t-Bu | 3-chloro-phenyl | 3-bromo-5-fluorophenyl | 2-fluoro-5-(CF$_3$)phenyl |
| CF$_3$ | 3-(CF$_3$)phenyl | 3-chloro-5-fluorophenyl | 2-fluoro-5-chlorophenyl |
| CH$_2$F | 3-fluoro-phenyl | 3-fluoro-4-chlorophenyl | 2,5-dichlorophenyl |
| CHF$_2$ | 3-cyano-phenyl | 2,4-dichlorophenyl | 2-fluoro-5-(OCF$_3$)phenyl |
| OMe | 3-(OCF$_3$)phenyl | 2,4-difluorophenyl | 2-chloro-5-(CF$_3$)phenyl |
| OEt | 4-fluoro-phenyl | 2-fluoro-4-cyanophenyl | |
| O-n-Pr | 4-chloro-phenyl | 2-fluoro-4-chlorophenyl | |
| O-i-Pr | 4-(CF$_3$)phenyl | 2-methyl-4-chlorophenyl | |

TABLE 2

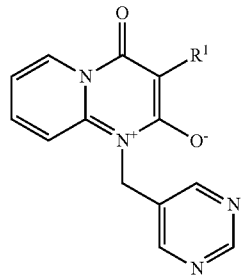

| $R^1$ | $R^1$ |
|---|---|
| 2-fluoro-4-pyridinyl | 2-chloro-4-pyridinyl |
| 2-bromo-4-pyridinyl | 2-(trifluoromethyl)-4-pyridinyl |
| 6-fluoro-2-pyridinyl | 6-chloro-2-pyridinyl |
| 6-bromo-2-pyridinyl | 6-(trifluoromethyl)-2-pyridinyl |
| 4-fluoro-2-pyridinyl | 4-chloro-2-pyridinyl |
| 4-bromo-2-pyridinyl | 4-(trifluoromethyl)-2-pyridinyl |

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids can be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which are branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention can also contain formulation auxiliaries and additives, known to those skilled in the art as formulation aids (some of which can be considered to also function as solid diluents, liquid diluents or surfactants). Such formulation auxiliaries and additives can control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| compound 1 | 98.5% |
| silica aerogel | 0.5% |
| synthetic amorphous fine silica | 1.0% |

Example B

| Wettable Powder | |
|---|---|
| compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| compound 3 | 10.0% |
| attapulgite granules (low volatile matter, 0.71/0.30 mm; U.S.S. No. 25-50 sieves) | 90.0% |

Example D

| Extruded Pellet | |
|---|---|
| compound 4 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| compound 5 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| compound 6 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| compound 7 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| compound 8 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
|---|---|
| compound 9 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| compound 10 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |

-continued

| Emulsion in Water | |
|---|---|
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| compound 11 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| compound 12 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal Bacillus thuringiensis toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests. Also the present compounds and compositions may interact synergistically with traits improving plant growth or other aspects of crop vigor, including traits conferring resistance to environmental stress such as suboptimal moisture.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hubner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cryptolestis ferrugineus*).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittela* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Ståal (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Note that some contemporary classification systems place Homoptera as a suborder within the order Hemiptera.

Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoptera frugiperda*).

Of note is use of compounds of this invention for controlling southern green stink bug (*Nezara viridula*), western tarnished plant bug (*Lygus hesperus*), rice water weevil (*Lissorhoptrus oryzophilus*), rice brown planthopper (*Nilaparvata lugens*), rice green leafhopper (*Nephotettix virescens*) and striped rice borer (*Chilo suppressalis*).

Compounds of the present invention are also useful for increasing vigor of a crop plant. This method comprises contacting the crop plant (e.g., foliage, flowers, fruit or roots) or the seed from which the crop plant is grown with a compound of Formula 1 in amount sufficient to achieve the desired plant vigor effect (i.e. biologically effective amount). Typically the compound of Formula 1 is applied in a formulated composition. Although the compound of Formula 1 is often applied directly to the crop plant or its seed, it can also be applied to the locus of the crop plant, i.e. the environment of the crop plant, particularly the portion of the environment in close enough proximity to allow the compound of Formula 1 to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula 1.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present invention can increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmiting plant pathogens such as viruses. Even in the absence of phytophagous invertebrate pests, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising one or more aspects adverse to the plant achieving the full genetic potential it would exhibit in an ideal environment.

Of note is the present method for increasing vigor of a crop plant wherein the crop plant is grown in an environment comprising phytophagous invertebrate pests. Also of note is the present method for increasing vigor of a crop plant wherein the crop plant is grown in an environment not comprising phytophagous invertebrate pests. Also of note is the present method for increasing vigor of a crop plant wherein the crop plant is grown an environment comprising an amount of moisture less than ideal for supporting growth of the crop plant. Of note is the present method for increasing vigor of a crop plant wherein the crop is rice. Also of note is the present method for increasing vigor of a crop plant wherein the crop is maize (corn). Also of note is the present method for increasing vigor of a crop plant wherein the crop is soybean.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide, or salt thereof, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bensultap, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, flpronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiocarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bensultap, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, flpronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, fluxapyroxad, folpet, fosetyl-aluminum, fthalide, fuberidazole, furalaxyl, furametpyr, hexaconazole, hymexazole, guazatine, imazalil, imibenconazole, iminoctadine, iodicarb, ipconazole, iprobenfos, iprodione, iprovalicarb, isoconazole, isoprothiolane, isotianil, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pryazophos, pyrifenox, pyrimethanil, pyrifenox, pyriofenone, pyrolnitrine, pyroquilon, quinconazole, quinoxyfen, quintozene, silthiofam, simeconazole, spiroxamine, streptomycin, sulfur, tebuconazole, tebufloquin, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamide, tricyclazole, trifloxystrobin, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

Of note are fungicides and compositions comprising fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, azoxystrobin, copper hydroxide, cymoxanil, cyproconazole, difenoconazole, famoxadone, fenoxanil, ferimzone, flusilazole, flutolanil, fthalide, furametpyr, hexaconazole, isoprothiolane, isotianil, kasugamycin, mancozeb, metominostrobin, orysastrobin, pencycuron, penthiopyrad, picoxystrobin, probenazole, propiconazole, proquinazid, pyroquilon, simeconazole, tiadinil, tricyclazole, trifloxystrobin and validamycin.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load. A greater-than-additive effect increasing crop plant vigor may also be observed.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual,* 13th Edition, C. D. S. Tomlin, Ed., British Crop Protection Council, Farnham, Surrey, U.K., 2003 and *The BioPesticide Manual,* $2^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1, an N-oxide, or salt thereof, is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which a compound of Formula 1 can be applied relative to an invertebrate pest control agent (e.g., "50:1 to 1:50" of a compound of Formula 1 relative to abamectin by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |

TABLE A-continued

| Invertebrate Pest Control Agent | Mode of Action or Chemical Class | Typical Weight Ratio |
|---|---|---|
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the Invertebrate Pest Control Agents listed in Table A above.

The weight ratios of a compound, including a compound of Formula 1, an N-oxide, or salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B19 are embodiments of specific compositions comprising a compound of Formula 1 (compound numbers (Cmpd. No.) refer to compounds in Index Table A) and an additional invertebrate pest control agent.

TABLE B1

| Mixture No. | Cmpd. No. | and | Invertebrate Pest Control Agent |
|---|---|---|---|
| B1-1 | 1 | and | Abamectin |
| B1-2 | 1 | and | Acetamiprid |
| B1-3 | 1 | and | Amitraz |
| B1-4 | 1 | and | Avermectin |
| B1-5 | 1 | and | Azadirachtin |
| B1-6 | 1 | and | Bensultap |
| B1-7 | 1 | and | Beta-cyfluthrin |
| B1-8 | 1 | and | Bifenthrin |
| B1-9 | 1 | and | Buprofezin |
| B1-10 | 1 | and | Cartap |
| B1-11 | 1 | and | Chlorantraniliprole |
| B1-12 | 1 | and | Chlorfenapyr |
| B1-13 | 1 | and | Chlorpyrifos |
| B1-14 | 1 | and | Clothianidin |
| B1-15 | 1 | and | Cyantraniliprole |
| B1-16 | 1 | and | Cyfluthrin |
| B1-17 | 1 | and | Cyhalothrin |
| B1-18 | 1 | and | Cypermethrin |
| B1-19 | 1 | and | Cyromazine |
| B1-20 | 1 | and | Deltamethrin |
| B1-21 | 1 | and | Dieldrin |
| B1-22 | 1 | and | Dinotefuran |
| B1-23 | 1 | and | Diofenolan |
| B1-24 | 1 | and | Emamectin |
| B1-25 | 1 | and | Endosulfan |
| B1-26 | 1 | and | Esfenvalerate |
| B1-27 | 1 | and | Ethiprole |
| B1-28 | 1 | and | Fenothiocarb |
| B1-29 | 1 | and | Fenoxycarb |
| B1-30 | 1 | and | Fenvalerate |
| B1-31 | 1 | and | Fipronil |
| B1-32 | 1 | and | Flonicamid |
| B1-33 | 1 | and | Flubendiamide |
| B1-34 | 1 | and | Flufenoxuron |
| B1-35 | 1 | and | Hexaflumuron |
| B1-36 | 1 | and | Hydramethylnon |
| B1-37 | 1 | and | Imidacloprid |
| B1-38 | 1 | and | Indoxacarb |
| B1-39 | 1 | and | Lambda-cyhalothrin |
| B1-40 | 1 | and | Lufenuron |
| B1-41 | 1 | and | Metaflumizone |
| B1-42 | 1 | and | Methomyl |
| B1-43 | 1 | and | Methoprene |

TABLE B1-continued

| Mixture No. | Cmpd. No. | and | Invertebrate Pest Control Agent |
|---|---|---|---|
| B1-44 | 1 | and | Methoxyfenozide |
| B1-45 | 1 | and | Nitenpyram |
| B1-46 | 1 | and | Nithiazine |
| B1-47 | 1 | and | Novaluron |
| B1-48 | 1 | and | Oxamyl |
| B1-49 | 1 | and | Phosmet |
| B1-50 | 1 | and | Pymetrozine |
| B1-51 | 1 | and | Pyrethrin |
| B1-52 | 1 | and | Pyridaben |
| B1-53 | 1 | and | Pyridalyl |
| B1-54 | 1 | and | Pyriproxyfen |
| B1-55 | 1 | and | Ryanodine |
| B1-56 | 1 | and | Spinetoram |
| B1-57 | 1 | and | Spinosad |
| B1-58 | 1 | and | Spirodiclofen |
| B1-59 | 1 | and | Spiromesifen |
| B1-60 | 1 | and | Spirotetramat |
| B1-61 | 1 | and | Sulfoxaflor |
| B1-62 | 1 | and | Tebufenozide |
| B1-63 | 1 | and | Tefluthrin |
| B1-64 | 1 | and | Thiacloprid |
| B1-65 | 1 | and | Thiamethoxam |
| B1-66 | 1 | and | Thiodicarb |
| B1-67 | 1 | and | Thiosultap-sodium |
| B1-68 | 1 | and | Tolfenpyrad |
| B1-69 | 1 | and | Tralomethrin |
| B1-70 | 1 | and | Triazamate |
| B1-71 | 1 | and | Triflumuron |
| B1-72 | 1 | and | *Bacillus thuringiensis* |
| B1-73 | 1 | and | *Bacillus thuringiensis* delta-endotoxin |
| B1-74 | 1 | and | NPV (e.g., Gemstar) |

Table B2

Table B2 is identical to Table B1, except that each reference to compound 1 in the column headed "Cmpd. No." is replaced by a reference to compound 2. For example, the first mixture in Table B2 is designated B2-1 and is a mixture of compound 2 and the additional invertebrate pest control agent abamectin.

Table B3

Table B3 is identical to Table B1, except that each reference to compound 1 in the column headed "Cmpd. No." is replaced by a reference to compound 3. For example, the first mixture in Table B3 is designated B3-1 and is a mixture of compound 3 and the additional invertebrate pest control agent abamectin.

Table B4

Table B4 is identical to Table B1, except that each reference to compound 1 in the column headed "Cmpd. No." is replaced by a reference to compound 4. For example, the first mixture in Table B4 is designated B4-1 and is a mixture of compound 4 and the additional invertebrate pest control agent abamectin.

Table B5

Table B5 is identical to Table B1, except that each reference to compound 1 in the column headed "Cmpd. No." is replaced by a reference to compound 5. For example, the first mixture in Table B5 is designated B5-1 and is a mixture of compound 5 and the additional invertebrate pest control agent abamectin.

Table B6

Table B6 is identical to Table B1, except that each reference to compound 1 in the column headed "Cmpd. No." is replaced by a reference to compound 6. For example, the first mixture in Table B6 is designated B6-1 and is a mixture of compound 6 and the additional invertebrate pest control agent abamectin.

Table B7

Table B7 is identical to Table B1, except that each reference to compound 1 in the column headed "Cmpd. No." is replaced by a reference to compound 7. For example, the first mixture in Table B7 is designated B7-1 and is a mixture of compound 7 and the additional invertebrate pest control agent abamectin.

Table B8

Table B8 is identical to Table B1, except that each reference to compound 1 in the column headed "Cmpd. No." is replaced by a reference to compound 8. For example, the first mixture in Table B8 is designated B8-1 and is a mixture of compound 8 and the additional invertebrate pest control agent abamectin.

Table B9

Table B9 is identical to Table B1, except that each reference to compound 1 in the column headed "Cmpd. No." is replaced by a reference to compound 9. For example, the first mixture in Table B9 is designated B9-1 and is a mixture of compound 9 and the additional invertebrate pest control agent abamectin.

Table B10

Table B10 is identical to Table B1, except that each reference to compound 1 in the column headed "Cmpd. No." is replaced by a reference to compound 10. For example, the first mixture in Table B 10 is designated B 10-1 and is a mixture of compound 10 and the additional invertebrate pest control agent abamectin.

Table B11

Table B11 is identical to Table B1, except that each reference to compound 1 in the column headed "Cmpd. No." is replaced by a reference to compound 11. For example, the first mixture in Table B 11 is designated B 11-1 and is a mixture of compound 11 and the additional invertebrate pest control agent abamectin.

Table B12

Table B12 is identical to Table B1, except that each reference to compound 1 in the column headed "Cmpd. No." is replaced by a reference to compound 12. For example, the first mixture in Table B 12 is designated B 12-1 and is a mixture of compound 12 and the additional invertebrate pest control agent abamectin.

Table B13

Table B13 is identical to Table B1, except that each reference to compound 1 in the column headed "Cmpd. No." is replaced by a reference to compound 13. For example, the first mixture in Table B13 is designated B13-1 and is a mixture of compound 13 and the additional invertebrate pest control agent abamectin.

Table B14

Table B14 is identical to Table B1, except that each reference to compound 1 in the column headed "Cmpd. No." is replaced by a reference to compound 14. For example, the first mixture in Table B 14 is designated B 14-1 and is a mixture of compound 14 and the additional invertebrate pest control agent abamectin.

Table B15

Table B15 is identical to Table B1, except that each reference to compound 1 in the column headed "Cmpd. No." is replaced by a reference to compound 15. For example, the first mixture in Table B15 is designated B15-1 and is a mixture of compound 15 and the additional invertebrate pest control agent abamectin.

Table B16

Table B16 is identical to Table B1, except that each reference to compound 1 in the column headed "Cmpd. No." is replaced by a reference to compound 16. For example, the first mixture in Table B 16 is designated B 16-1 and is a mixture of compound 16 and the additional invertebrate pest control agent abamectin.

Table B17

Table B17 is identical to Table B1, except that each reference to compound 1 in the column headed "Cmpd. No." is replaced by a reference to compound 17. For example, the first mixture in Table B 17 is designated B 17-1 and is a mixture of compound 17 and the additional invertebrate pest control agent abamectin.

Table B18

Table B18 is identical to Table B1, except that each reference to compound 1 in the column headed "Cmpd. No." is replaced by a reference to compound 18. For example, the first mixture in Table B18 is designated B18-1 and is a mixture of compound 18 and the additional invertebrate pest control agent abamectin.

Table B19

Table B19 is identical to Table B1, except that each reference to compound 1 in the column headed "Cmpd. No." is replaced by a reference to compound 19. For example, the first mixture in Table B 18 is designated B 19-1 and is a mixture of compound 19 and the additional invertebrate pest control agent abamectin.

The specific mixtures listed in Tables B1 to B19 typically combine a compound of Formula 1 with the other invertebrate pest agent in the ratios specified in Table A.

Listed below in Tables C1 to C19 are specific mixtures comprising a compound of Formula 1 (compound numbers (Cmpd. No.) refer to compounds in Index Table A) and an additional invertebrate pest control agent. Tables C1 to C19 further list specific weight ratios typical of the mixtures of Tables C 1 to C19. For example, the first weight ratio entry of the first line of Table C1 specifically discloses the mixture of Compound 1 of Index Table A with abamectin applied in a weight ratio of 100 parts Compound 1 to 1 part abamectin.

TABLE C1

| Mixture No. | Cmpd. No. | and | Invertebrate Pest Control Agent | Typical Mixture Ratios (by weight) | | | | | | | |
|---|---|---|---|---|---|---|---|---|---|---|---|
| C1-1 | 1 | and | Abamectin | 100:1 | 10:1 | 5:1 | 2:1 | 1:1 | 1:2 | 1:5 | 1:10 | 1:100 |
| C1-2 | 1 | and | Acetamiprid | 100:1 | 10:1 | 5:1 | 2:1 | 1:1 | 1:2 | 1:5 | 1:10 | 1:100 |
| C1-3 | 1 | and | Amitraz | 100:1 | 10:1 | 5:1 | 2:1 | 1:1 | 1:2 | 1:5 | 1:10 | 1:100 |
| C1-4 | 1 | and | Avermectin | 100:1 | 10:1 | 5:1 | 2:1 | 1:1 | 1:2 | 1:5 | 1:10 | 1:100 |
| C1-5 | 1 | and | Azadirachtin | 100:1 | 10:1 | 5:1 | 2:1 | 1:1 | 1:2 | 1:5 | 1:10 | 1:100 |
| C1-6 | 1 | and | Bensultap | 100:1 | 10:1 | 5:1 | 2:1 | 1:1 | 1:2 | 1:5 | 1:10 | 1:100 |
| C1-7 | 1 | and | Beta-cyfluthrin | 100:1 | 10:1 | 5:1 | 2:1 | 1:1 | 1:2 | 1:5 | 1:10 | 1:100 |
| C1-8 | 1 | and | Bifenthrin | 100:1 | 10:1 | 5:1 | 2:1 | 1:1 | 1:2 | 1:5 | 1:10 | 1:100 |
| C1-9 | 1 | and | Buprofezin | 100:1 | 10:1 | 5:1 | 2:1 | 1:1 | 1:2 | 1:5 | 1:10 | 1:100 |
| C1-10 | 1 | and | Cartap | 100:1 | 10:1 | 5:1 | 2:1 | 1:1 | 1:2 | 1:5 | 1:10 | 1:100 |
| C1-11 | 1 | and | Chlorantraniliprole | 100:1 | 10:1 | 5:1 | 2:1 | 1:1 | 1:2 | 1:5 | 1:10 | 1:100 |
| C1-12 | 1 | and | Chlorfenapyr | 100:1 | 10:1 | 5:1 | 2:1 | 1:1 | 1:2 | 1:5 | 1:10 | 1:100 |
| C1-13 | 1 | and | Chlorpyrifos | 100:1 | 10:1 | 5:1 | 2:1 | 1:1 | 1:2 | 1:5 | 1:10 | 1:100 |
| C1-14 | 1 | and | Clothianidin | 100:1 | 10:1 | 5:1 | 2:1 | 1:1 | 1:2 | 1:5 | 1:10 | 1:100 |
| C1-15 | 1 | and | Cyantraniliprole | 100:1 | 10:1 | 5:1 | 2:1 | 1:1 | 1:2 | 1:5 | 1:10 | 1:100 |
| C1-16 | 1 | and | Cyfluthrin | 100:1 | 10:1 | 5:1 | 2:1 | 1:1 | 1:2 | 1:5 | 1:10 | 1:100 |
| C1-17 | 1 | and | Cyhalothrin | 100:1 | 10:1 | 5:1 | 2:1 | 1:1 | 1:2 | 1:5 | 1:10 | 1:100 |
| C1-18 | 1 | and | Cypermethrin | 100:1 | 10:1 | 5:1 | 2:1 | 1:1 | 1:2 | 1:5 | 1:10 | 1:100 |
| C1-19 | 1 | and | Cyromazine | 100:1 | 10:1 | 5:1 | 2:1 | 1:1 | 1:2 | 1:5 | 1:10 | 1:100 |
| C1-20 | 1 | and | Deltamethrin | 100:1 | 10:1 | 5:1 | 2:1 | 1:1 | 1:2 | 1:5 | 1:10 | 1:100 |
| C1-21 | 1 | and | Dieldrin | 100:1 | 10:1 | 5:1 | 2:1 | 1:1 | 1:2 | 1:5 | 1:10 | 1:100 |
| C1-22 | 1 | and | Dinotefuran | 100:1 | 10:1 | 5:1 | 2:1 | 1:1 | 1:2 | 1:5 | 1:10 | 1:100 |
| C1-23 | 1 | and | Diofenolan | 100:1 | 10:1 | 5:1 | 2:1 | 1:1 | 1:2 | 1:5 | 1:10 | 1:100 |
| C1-24 | 1 | and | Emamectin | 100:1 | 10:1 | 5:1 | 2:1 | 1:1 | 1:2 | 1:5 | 1:10 | 1:100 |
| C1-25 | 1 | and | Endosulfan | 100:1 | 10:1 | 5:1 | 2:1 | 1:1 | 1:2 | 1:5 | 1:10 | 1:100 |
| C1-26 | 1 | and | Esfenvalerate | 100:1 | 10:1 | 5:1 | 2:1 | 1:1 | 1:2 | 1:5 | 1:10 | 1:100 |
| C1-27 | 1 | and | Ethiprole | 100:1 | 10:1 | 5:1 | 2:1 | 1:1 | 1:2 | 1:5 | 1:10 | 1:100 |
| C1-28 | 1 | and | Fenothiocarb | 100:1 | 10:1 | 5:1 | 2:1 | 1:1 | 1:2 | 1:5 | 1:10 | 1:100 |
| C1-29 | 1 | and | Fenoxycarb | 100:1 | 10:1 | 5:1 | 2:1 | 1:1 | 1:2 | 1:5 | 1:10 | 1:100 |
| C1-30 | 1 | and | Fenvalerate | 100:1 | 10:1 | 5:1 | 2:1 | 1:1 | 1:2 | 1:5 | 1:10 | 1:100 |
| C1-31 | 1 | and | Fipronil | 100:1 | 10:1 | 5:1 | 2:1 | 1:1 | 1:2 | 1:5 | 1:10 | 1:100 |
| C1-32 | 1 | and | Flonicamid | 100:1 | 10:1 | 5:1 | 2:1 | 1:1 | 1:2 | 1:5 | 1:10 | 1:100 |
| C1-33 | 1 | and | Flubendiamide | 100:1 | 10:1 | 5:1 | 2:1 | 1:1 | 1:2 | 1:5 | 1:10 | 1:100 |

TABLE C1-continued

| Mixture No. | Cmpd. No. | and | Invertebrate Pest Control Agent | Typical Mixture Ratios (by weight) | | | | | | | |
|---|---|---|---|---|---|---|---|---|---|---|---|
| C1-34 | 1 | and | Flufenoxuron | 100:1 | 10:1 | 5:1 | 2:1 | 1:1 | 1:2 | 1:5 | 1:10 | 1:100 |
| C1-35 | 1 | and | Hexaflumuron | 100:1 | 10:1 | 5:1 | 2:1 | 1:1 | 1:2 | 1:5 | 1:10 | 1:100 |
| C1-36 | 1 | and | Hydramethylnon | 100:1 | 10:1 | 5:1 | 2:1 | 1:1 | 1:2 | 1:5 | 1:10 | 1:100 |
| C1-37 | 1 | and | Imidacloprid | 100:1 | 10:1 | 5:1 | 2:1 | 1:1 | 1:2 | 1:5 | 1:10 | 1:100 |
| C1-38 | 1 | and | Indoxacarb | 100:1 | 10:1 | 5:1 | 2:1 | 1:1 | 1:2 | 1:5 | 1:10 | 1:100 |
| C1-39 | 1 | and | Lambda-cyhalothrin | 100:1 | 10:1 | 5:1 | 2:1 | 1:1 | 1:2 | 1:5 | 1:10 | 1:100 |
| C1-40 | 1 | and | Lufenuron | 100:1 | 10:1 | 5:1 | 2:1 | 1:1 | 1:2 | 1:5 | 1:10 | 1:100 |
| C1-41 | 1 | and | Metaflumizone | 100:1 | 10:1 | 5:1 | 2:1 | 1:1 | 1:2 | 1:5 | 1:10 | 1:100 |
| C1-42 | 1 | and | Methomyl | 100:1 | 10:1 | 5:1 | 2:1 | 1:1 | 1:2 | 1:5 | 1:10 | 1:100 |
| C1-43 | 1 | and | Methoprene | 100:1 | 10:1 | 5:1 | 2:1 | 1:1 | 1:2 | 1:5 | 1:10 | 1:100 |
| C1-44 | 1 | and | Methoxyfenozide | 100:1 | 10:1 | 5:1 | 2:1 | 1:1 | 1:2 | 1:5 | 1:10 | 1:100 |
| C1-45 | 1 | and | Nitenpyram | 100:1 | 10:1 | 5:1 | 2:1 | 1:1 | 1:2 | 1:5 | 1:10 | 1:100 |
| C1-46 | 1 | and | Nithiazine | 100:1 | 10:1 | 5:1 | 2:1 | 1:1 | 1:2 | 1:5 | 1:10 | 1:100 |
| C1-47 | 1 | and | Novaluron | 100:1 | 10:1 | 5:1 | 2:1 | 1:1 | 1:2 | 1:5 | 1:10 | 1:100 |
| C1-48 | 1 | and | Oxamyl | 100:1 | 10:1 | 5:1 | 2:1 | 1:1 | 1:2 | 1:5 | 1:10 | 1:100 |
| C1-49 | 1 | and | Phosmet | 100:1 | 10:1 | 5:1 | 2:1 | 1:1 | 1:2 | 1:5 | 1:10 | 1:100 |
| C1-50 | 1 | and | Pymetrozine | 100:1 | 10:1 | 5:1 | 2:1 | 1:1 | 1:2 | 1:5 | 1:10 | 1:100 |
| C1-51 | 1 | and | Pyrethrin | 100:1 | 10:1 | 5:1 | 2:1 | 1:1 | 1:2 | 1:5 | 1:10 | 1:100 |
| C1-52 | 1 | and | Pyridaben | 100:1 | 10:1 | 5:1 | 2:1 | 1:1 | 1:2 | 1:5 | 1:10 | 1:100 |
| C1-53 | 1 | and | Pyridalyl | 100:1 | 10:1 | 5:1 | 2:1 | 1:1 | 1:2 | 1:5 | 1:10 | 1:100 |
| C1-54 | 1 | and | Pyriproxyfen | 100:1 | 10:1 | 5:1 | 2:1 | 1:1 | 1:2 | 1:5 | 1:10 | 1:100 |
| C1-55 | 1 | and | Ryanodine | 100:1 | 10:1 | 5:1 | 2:1 | 1:1 | 1:2 | 1:5 | 1:10 | 1:100 |
| C1-56 | 1 | and | Spinetoram | 100:1 | 10:1 | 5:1 | 2:1 | 1:1 | 1:2 | 1:5 | 1:10 | 1:100 |
| C1-57 | 1 | and | Spinosad | 100:1 | 10:1 | 5:1 | 2:1 | 1:1 | 1:2 | 1:5 | 1:10 | 1:100 |
| C1-58 | 1 | and | Spirodiclofen | 100:1 | 10:1 | 5:1 | 2:1 | 1:1 | 1:2 | 1:5 | 1:10 | 1:100 |
| C1-59 | 1 | and | Spiromesifen | 100:1 | 10:1 | 5:1 | 2:1 | 1:1 | 1:2 | 1:5 | 1:10 | 1:100 |
| C1-60 | 1 | and | Spirotetramat | 100:1 | 10:1 | 5:1 | 2:1 | 1:1 | 1:2 | 1:5 | 1:10 | 1:100 |
| C1-61 | 1 | and | Sulfoxaflor | 100:1 | 10:1 | 5:1 | 2:1 | 1:1 | 1:2 | 1:5 | 1:10 | 1:100 |
| C1-62 | 1 | and | Tebufenozide | 100:1 | 10:1 | 5:1 | 2:1 | 1:1 | 1:2 | 1:5 | 1:10 | 1:100 |
| C1-63 | 1 | and | Tefluthrin | 100:1 | 10:1 | 5:1 | 2:1 | 1:1 | 1:2 | 1:5 | 1:10 | 1:100 |
| C1-64 | 1 | and | Thiacloprid | 100:1 | 10:1 | 5:1 | 2:1 | 1:1 | 1:2 | 1:5 | 1:10 | 1:100 |
| C1-65 | 1 | and | Thiamethoxam | 100:1 | 10:1 | 5:1 | 2:1 | 1:1 | 1:2 | 1:5 | 1:10 | 1:100 |
| C1-66 | 1 | and | Thiodicarb | 100:1 | 10:1 | 5:1 | 2:1 | 1:1 | 1:2 | 1:5 | 1:10 | 1:100 |
| C1-67 | 1 | and | Thiosultap-sodium | 100:1 | 10:1 | 5:1 | 2:1 | 1:1 | 1:2 | 1:5 | 1:10 | 1:100 |
| C1-68 | 1 | and | Tolfenpyrad | 100:1 | 10:1 | 5:1 | 2:1 | 1:1 | 1:2 | 1:5 | 1:10 | 1:100 |
| C1-69 | 1 | and | Tralomethrin | 100:1 | 10:1 | 5:1 | 2:1 | 1:1 | 1:2 | 1:5 | 1:10 | 1:100 |
| C1-70 | 1 | and | Triazamate | 100:1 | 10:1 | 5:1 | 2:1 | 1:1 | 1:2 | 1:5 | 1:10 | 1:100 |
| C1-71 | 1 | and | Triflumuron | 100:1 | 10:1 | 5:1 | 2:1 | 1:1 | 1:2 | 1:5 | 1:10 | 1:100 |
| C1-72 | 1 | and | *Bacillus thuringiensis* | 100:1 | 10:1 | 5:1 | 2:1 | 1:1 | 1:2 | 1:5 | 1:10 | 1:100 |
| C1-73 | 1 | and | *Bacillus thuringiensis* delta-endotoxin | 100:1 | 10:1 | 5:1 | 2:1 | 1:1 | 1:2 | 1:5 | 1:10 | 1:100 |
| C1-74 | 1 | and | NPV (e.g., Gemstar) | 100:1 | 10:1 | 5:1 | 2:1 | 1:1 | 1:2 | 1:5 | 1:10 | 1:100 |

Table C2

Table C2 is identical to Table C1, except that each reference to compound 1 in the column headed "Cmpd. No." is replaced by a reference to compound 2. For example, the first weight ratio entry of the first line of Table C2 specifically discloses the mixture of Compound 1 of Index Table A with abamectin applied in a weight ratio of 100 parts Compound 1 to 1 part abamectin.

Table C3

Table C3 is identical to Table C1, except that each reference to compound 1 in the column headed "Cmpd. No." is replaced by a reference to compound 3. For example, the first weight ratio entry of the first line of Table C3 specifically discloses the mixture of Compound 3 of Index Table A with abamectin applied in a weight ratio of 100 parts Compound 3 to 1 part abamectin.

Table C4

Table C4 is identical to Table C1, except that each reference to compound 1 in the column headed "Cmpd. No." is replaced by a reference to compound 4. For example, the first weight ratio entry of the first line of Table C4 specifically discloses the mixture of Compound 4 of Index Table A with abamectin applied in a weight ratio of 100 parts Compound 4 to 1 part abamectin.

Table C5

Table C5 is identical to Table C1, except that each reference to compound 1 in the column headed "Cmpd. No." is replaced by a reference to compound 5. For example, the first weight ratio entry of the first line of Table C5 specifically discloses the mixture of Compound 5 of Index Table A with abamectin applied in a weight ratio of 100 parts Compound 5 to 1 part abamectin.

Table C6

Table C6 is identical to Table C1, except that each reference to compound 1 in the column headed "Cmpd. No." is replaced by a reference to compound 6. For example, the first weight ratio entry of the first line of Table C6 specifically discloses the mixture of Compound 6 of Index Table A with abamectin applied in a weight ratio of 100 parts Compound 6 to 1 part abamectin.

Table C7

Table C7 is identical to Table C1, except that each reference to compound 1 in the column headed "Cmpd. No." is replaced by a reference to compound 7. For example, the first weight ratio entry of the first line of Table C7 specifically discloses the mixture of Compound 7 of Index Table A with abamectin applied in a weight ratio of 100 parts Compound 7 to 1 part abamectin.

Table C8

Table C8 is identical to Table C1, except that each reference to compound 1 in the column headed "Cmpd. No." is replaced by a reference to compound 8. For example, the first weight ratio entry of the first line of Table C8 specifically discloses the mixture of Compound 8 of Index Table A with abamectin applied in a weight ratio of 100 parts Compound 8 to 1 part abamectin.

Table C9

Table C9 is identical to Table C1, except that each reference to compound 1 in the column headed "Cmpd. No." is replaced by a reference to compound 9. For example, the first weight ratio entry of the first line of Table C9 specifically discloses the mixture of Compound 9 of Index Table A with abamectin applied in a weight ratio of 100 parts Compound 9 to 1 part abamectin.

Table C10

Table C 10 is identical to Table C1, except that each reference to compound 1 in the column headed "Cmpd. No." is replaced by a reference to compound 10. For example, the first weight ratio entry of the first line of Table C 10 specifically discloses the mixture of Compound 10 of Index Table A with abamectin applied in a weight ratio of 100 parts Compound 10 to 1 part abamectin.

Table C11

Table C11 is identical to Table C1, except that each reference to compound 1 in the column headed "Cmpd. No." is replaced by a reference to compound 11. For example, the first weight ratio entry of the first line of Table C11 specifically discloses the mixture of Compound 11 of Index Table A with abamectin applied in a weight ratio of 100 parts Compound 11 to 1 part abamectin.

Table C12

Table C 12 is identical to Table C1, except that each reference to compound 1 in the column headed "Cmpd. No." is replaced by a reference to compound 12. For example, the first weight ratio entry of the first line of Table C 12 specifically discloses the mixture of Compound 12 of Index Table A with abamectin applied in a weight ratio of 100 parts Compound 12 to 1 part abamectin.

Table C13

Table C 13 is identical to Table C1, except that each reference to compound 1 in the column headed "Cmpd. No." is replaced by a reference to compound 13. For example, the first weight ratio entry of the first line of Table C 13 specifically discloses the mixture of Compound 13 of Index Table A with abamectin applied in a weight ratio of 100 parts Compound 13 to 1 part abamectin.

Table C14

Table C14 is identical to Table C1, except that each reference to compound 1 in the column headed "Cmpd. No." is replaced by a reference to compound 14. For example, the first weight ratio entry of the first line of Table C14 specifically discloses the mixture of Compound 14 of Index Table A with abamectin applied in a weight ratio of 100 parts Compound 14 to 1 part abamectin.

Table C15

Table C 15 is identical to Table C1, except that each reference to compound 1 in the column headed "Cmpd. No." is replaced by a reference to compound 15. For example, the first weight ratio entry of the first line of Table C 15 specifically discloses the mixture of Compound 15 of Index Table A with abamectin applied in a weight ratio of 100 parts Compound 15 to 1 part abamectin.

Table C16

Table C 16 is identical to Table C1, except that each reference to compound 1 in the column headed "Cmpd. No." is replaced by a reference to compound 16. For example, the first weight ratio entry of the first line of Table C 16 specifically discloses the mixture of Compound 16 of Index Table A with abamectin applied in a weight ratio of 100 parts Compound 16 to 1 part abamectin.

Table C17

Table C 17 is identical to Table C1, except that each reference to compound 1 in the column headed "Cmpd. No." is replaced by a reference to compound 17. For example, the first weight ratio entry of the first line of Table C 17 specifically discloses the mixture of Compound 17 of Index Table A with abamectin applied in a weight ratio of 100 parts Compound 17 to 1 part abamectin.

Table C18

Table C 18 is identical to Table C1, except that each reference to compound 1 in the column headed "Cmpd. No." is replaced by a reference to compound 18. For example, the first weight ratio entry of the first line of Table C 18 specifically discloses the mixture of Compound 18 of Index Table A with abamectin applied in a weight ratio of 100 parts Compound 18 to 1 part abamectin.

Table C19

Table C 19 is identical to Table C1, except that each reference to compound 1 in the column headed "Cmpd. No." is replaced by a reference to compound 19. For example, the first weight ratio entry of the first line of Table C 19 specifically discloses the mixture of Compound 19 of Index Table A with abamectin applied in a weight ratio of 100 parts Compound 19 to 1 part abamectin.

Listed below in Tables D1 to D19 are embodiments of specific compositions comprising a compound of Formula 1

(compound numbers (Cmpd. No.) refer to compounds in Index Table A) and an additional fungicide.

TABLE D1

| Mixture No. | Cmpd. No. | and | Fungicide |
|---|---|---|---|
| D1-1 | 1 | and | Probenazole |
| D1-2 | 1 | and | Tiadinil |
| D1-3 | 1 | and | Isotianil |
| D1-4 | 1 | and | Pyroquilon |
| D1-5 | 1 | and | Metominostrobin |
| D1-6 | 1 | and | Flutolanil |
| D1-7 | 1 | and | Validamycin |
| D1-8 | 1 | and | Furametpyr |
| D1-9 | 1 | and | Pencycuron |
| D1-10 | 1 | and | Simeconazole |
| D1-11 | 1 | and | Orysastrobin |
| D1-12 | 1 | and | Trifloxystrobin |
| D1-13 | 1 | and | Isoprothiolane |
| D1-14 | 1 | and | Azoxystrobin |
| D1-15 | 1 | and | Tricyclazole |
| D1-16 | 1 | and | Hexaconazole |
| D1-17 | 1 | and | Difenoconazole |
| D1-18 | 1 | and | Cyproconazole |
| D1-19 | 1 | and | Propiconazole |
| D1-20 | 1 | and | Fenoxanil |
| D1-21 | 1 | and | Ferimzone |
| D1-22 | 1 | and | Fthalide |
| D1-23 | 1 | and | Kasugamycin |
| D1-24 | 1 | and | Picoxystrobin |
| D1-25 | 1 | and | Penthiopyrad |
| D1-26 | 1 | and | Famoxadone |
| D1-27 | 1 | and | Cymoxanil |
| D1-28 | 1 | and | Proquinazid |
| D1-29 | 1 | and | Flusilazole |
| D1-30 | 1 | and | Mancozeb |
| D1-31 | 1 | and | Copper hydroxide |
| D1-32 | 1 | and | (a) |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Table D2

Table D2 is identical to Table D1, except that each reference to compound 1 in the column headed "Cmpd. No." is replaced by a reference to compound 2. For example, the first mixture in Table D2 is designated D2-1 and is a mixture of compound 2 and the additional fungicide probenazole.

Table D3

Table D3 is identical to Table D1, except that each reference to compound 1 in the column headed "Cmpd. No." is replaced by a reference to compound 3. For example, the first mixture in Table D3 is designated D3-1 and is a mixture of compound 3 and the additional fungicide probenazole.

Table D4

Table D4 is identical to Table D1, except that each reference to compound 1 in the column headed "Cmpd. No." is replaced by a reference to compound 4. For example, the first mixture in Table D4 is designated D4-1 and is a mixture of compound 4 and the additional fungicide probenazole.

Table D5

Table D5 is identical to Table D1, except that each reference to compound 1 in the column headed "Cmpd. No." is replaced by a reference to compound 5. For example, the first mixture in Table D5 is designated D5-1 and is a mixture of compound 5 and the additional fungicide probenazole.

Table D6

Table D6 is identical to Table D1, except that each reference to compound 1 in the column headed "Cmpd. No." is replaced by a reference to compound 6. For example, the first mixture in Table D6 is designated D6-1 and is a mixture of compound 6 and the additional fungicide probenazole.

Table D7

Table D7 is identical to Table D1, except that each reference to compound 1 in the column headed "Cmpd. No." is replaced by a reference to compound 7. For example, the first mixture in Table D7 is designated D7-1 and is a mixture of compound 7 and the additional fungicide probenazole.

Table D8

Table D8 is identical to Table D1, except that each reference to compound 1 in the column headed "Cmpd. No." is replaced by a reference to compound 8. For example, the first mixture in Table D8 is designated D8-1 and is a mixture of compound 8 and the additional fungicide probenazole.

Table D9

Table D9 is identical to Table D1, except that each reference to compound 1 in the column headed "Cmpd. No." is replaced by a reference to compound 9. For example, the first mixture in Table D9 is designated D9-1 and is a mixture of compound 9 and the additional fungicide probenazole.

Table D10

Table D10 is identical to Table D1, except that each reference to compound 1 in the column headed "Cmpd. No." is replaced by a reference to compound 10. For example, the first mixture in Table D10 is designated D10-1 and is a mixture of compound 10 and the additional fungicide probenazole.

Table D11

Table D11 is identical to Table D1, except that each reference to compound 1 in the column headed "Cmpd. No." is replaced by a reference to compound 11. For example, the first mixture in Table D11 is designated D11-1 and is a mixture of compound 11 and the additional fungicide probenazole.

Table D12

Table D12 is identical to Table D1, except that each reference to compound 1 in the column headed "Cmpd. No." is replaced by a reference to compound 12. For example, the first mixture in Table D12 is designated D12-1 and is a mixture of compound 12 and the additional fungicide probenazole.

Table D13

Table D13 is identical to Table D1, except that each reference to compound 1 in the column headed "Cmpd. No." is replaced by a reference to compound 13. For example, the first mixture in Table D13 is designated D13-1 and is a mixture of compound 13 and the additional fungicide probenazole.

Table D14

Table D14 is identical to Table D1, except that each reference to compound 1 in the column headed "Cmpd. No." is replaced by a reference to compound 14. For example, the first mixture in Table D14 is designated D14-1 and is a mixture of compound 14 and the additional fungicide probenazole.

Table D15

Table D15 is identical to Table D1, except that each reference to compound 1 in the column headed "Cmpd. No." is replaced by a reference to compound 15. For example, the first mixture in Table D15 is designated D15-1 and is a mixture of compound 15 and the additional fungicide probenazole.

Table D16

Table D16 is identical to Table D1, except that each reference to compound 1 in the column headed "Cmpd. No." is replaced by a reference to compound 16. For example, the first mixture in Table D16 is designated D16-1 and is a mixture of compound 16 and the additional fungicide probenazole.

Table D17

Table D17 is identical to Table D1, except that each reference to compound 1 in the column headed "Cmpd. No." is replaced by a reference to compound 17. For example, the first mixture in Table D17 is designated D17-1 and is a mixture of compound 17 and the additional fungicide probenazole.

Table D18

Table D18 is identical to Table D1, except that each reference to compound 1 in the column headed "Cmpd. No." is replaced by a reference to compound 18. For example, the first mixture in Table D18 is designated D18-1 and is a mixture of compound 18 and the additional fungicide probenazole.

Table D19

Table D19 is identical to Table D1, except that each reference to compound 1 in the column headed "Cmpd. No." is replaced by a reference to compound 19. For example, the first mixture in Table D19 is designated D19-1 and is a mixture of compound 19 and the additional fungicide probenazole.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

Embodiments of the method of this invention include contacting the environment. Of note is the method wherein the environment is a plant. Also of note is the method wherein the environment is an animal. Also of note is the method wherein the environment is a seed.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Monograph No. 57, and references listed therein.

Compounds of Formula 1 and their compositions, both alone and in combination with other insecticides and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides with which compounds of Formula 1 can be formulated to provide mixtures useful in seed treatment include abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

Fungicides with which compounds of Formula 1 can be formulated to provide mixtures useful in seed treatment include amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising compounds of Formula 1 useful for seed treatment can further comprise bacteria such as *Bacillus pumilus* (e.g., strain GB34) and *Bacillus firmus* (e.g., isolate 1582), rhizobia inoculants/extenders, isoflavonoids and lipo-chitooligosaccharides.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1 an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control. Biologically effective amounts for increasing plant vigor are generally similar to biologically effective amounts for invertebrate pest control, and optimal amounts to achieve particular aspects of plant vigor enhancement can determined through simple experimentation.

Representative compounds of this invention prepared by the methods described herein are shown in Index Table A. See Index Table B for $^1$H NMR data. For mass spectral data (AP$^+$ (M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported.

The following abbreviations are used in the Index Tables which follow: Cmpd means Compound.

INDEX TABLE A

| Cmpd | R$^1$ | m.p. (° C.) | AP$^+$ (M + 1) |
|---|---|---|---|
| 1 | phenyl | 211-212 | |
| 2 | 4-fluorophenyl | | 349 |
| 3 | 3-(trifluoromethyl)phenyl | 183-185 | |
| 4 | 2-methoxyphenyl | | 361 |
| 5 | 3-methoxyphenyl | | 361 |
| 6 | 2,4-difluorophenyl | * | |
| 7 | 3-(trifluoromethoxy)phenyl | | 415 |
| 8 | 3-bromophenyl | * | |
| 9 | 2-fluorophenyl | | 349 |

INDEX TABLE A-continued

| Cmpd | R$^1$ | m.p. (° C.) | AP$^+$ (M + 1) |
|---|---|---|---|
| 10 | 2-fluoro-5-(trifluoromethyl)phenyl | * | |
| 11 | 3-methylphenyl | * | |
| 12 | 4-fluoro-3-(trifluoromethyl)phenyl | | 417 |
| 13 | 4-chloro-2-fluorophenyl | | 459 |
| 14 | 2-chlorophenyl | | 365 |
| 15 | 3-chloro-5-(trifluoromethyl)phenyl | | 433 |
| 16 | 3,5-dichlorophenyl | | 399 |
| 17 | 3,5-dichloro-4-fluorophenyl | | 417 |
| 18 | 4'-cyano-5,2'-dimethyl[1,1'-biphenyl]-3-yl | | 460 |
| 19 | 3-chlorophenyl | * | |

* See Index Table B for $^1$H NMR data.

INDEX TABLE B

| Cmpd | $^1$H NMR Data$^a$ |
|---|---|
| 6 | (acetone-d$_6$) δ 9.41 (d, 1H), 9.07 (s, 1H), 8.89 (s, 2H), 8.36 (t, 1H), 7.96 (d, 1H), 7.56-7.58 (m, 2H), 6.96-7.00 (m, 2H), 5.74 (s, 2H). |
| 8 | (acetone-d$_6$) δ 9.47 (d, 1H), 9.07 (s, 1H), 8.90 (s, 2H), 8.36 (t, 1H), 8.19 (s, 1H), 7.93-7.95 (m, 2H), 7.59 (t, 1H), 7.24-7.30 (m, 2H), 5.76 (s, 2H). |
| 10 | (acetone-d$_6$) δ 9.43 (d, 1H), 9.07 (s, 1H), 8.90 (s, 2H), 8.39 (t, 1H), 7.98 (d, 1H), 7.95 (dd, 1H), 7.64-7.68 (m, 1H), 7.60 (t, 1H), 7.35 (t, 1H), 5.76 (s, 2H). |
| 11 | (dmso-d$_6$) δ 9.33 (d, 1H), 9.11 (s, 1H), 8.82 (s, 2H), 8.27 (t, 1H), 7.87 (d, 1H), 7.47-7.54 (m, 2H), 7.26 (t, 1H), 6.99 (d, 1H), 5.59 (s, 2H), 2.31 (s, 3H). |
| 19 | (dmso-d$_6$) δ 9.34 (d, 1H), 9.11 (s, 1H), 8.83 (s, 2H), 8.29 (dt, 1H), 7.77-7.88 (m, 3H), 7.55 (dt, 1H), 7.32-7.36 (m, 1H), 7.23 (d, 1H), 5.60 (s, 2H). |

$^a$$^1$H NMR data are in ppm downfield from tetramethylsilane. CDCl$_3$ solution unless indicated otherwise; "acetone-d$_6$" is CD$_3$C(═O)CD$_3$, "dmso-d$_6$" is CD$_3$S(═O)CD$_3$. Couplings are designated by (s)-singlet, (d)-doublet, (t)-triplet, (m)-multiplet, (dd)-doublet of doublets, (dt)-doublet of triplets, (br s)-broad singlet.

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. Compound numbers refer to compounds in Index Table A.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with ~50 neonate larvae that were dispensed into the test unit via corn cob grits using a bazooka inoculator. The larvae moved onto the test plant after being dispensed into the test unit.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co., Wheaton, Ill., USA) positioned 1.27 cm (0.5 inches) above the top of each test unit. Test compounds were sprayed at 250, 50 and/or 10 ppm, and replicated three times. After spraying of the formulated test compound, each test unit was allowed to dry for 1 h and then a black, screened cap was placed on top. The test units were held for 6 days in a growth chamber at 25° C. and 70% relative humidity. Plant feeding damage was then visually assessed based on foliage consumed.

Of the compounds of Formula 1 tested at 250 ppm, the following provided very good to excellent levels of control efficacy (40% or less feeding damage and/or 100% mortality): 1, 3, 4, 7, 8, 13 and 15.

Of the compounds of Formula 1 tested at 50 ppm, the following provided very good to excellent levels of control efficacy (40% or less feeding damage and/or 100% mortality): 1, 3, 4, 5, 8 and 19.

Of the compounds of Formula 1 tested at 10 ppm, the following provided very good to excellent levels of control efficacy (40% or less feeding damage and/or 100% mortality): 7, 15, 16 and 17.

Test B

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250, 50 and/or 10 ppm as described for Test A. The applications were replicated three times. After spraying of the formulated test compound, each test unit was allowed to dry for 1 h and then a black, screened cap was placed on top. The test units were held for 6 days in a growth chamber at 19-21° C. and 50-70% relative humidity. Each test unit was then visually assessed for insect mortality.

Of the compounds of Formula 1 tested at 250 ppm, the following resulted in at least 80% mortality: 1 and 3.

Of the compounds of Formula 1 tested at 50 ppm, the following resulted in at least 80% mortality: 1, 3, 15, 16 and 19.

Of the compounds of Formula 1 tested at 10 ppm, the following resulted in at least 80% mortality: 15.

Test C

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test B, and the soil of the test unit was covered with a layer of sand.

Test compounds were formulated and sprayed at 250 and/or 50 ppm as described for Test B. The applications were replicated three times. After spraying, the test units were maintained in a growth chamber and then visually rated as described for Test C.

Of the compounds of Formula 1 tested at 250 ppm, the following resulted in at least 80% mortality: 1 and 3.

Of the compounds of Formula 1 tested at 50 ppm, the following resulted in at least 80% mortality: 3, 7 and 12.

Test D

For evaluating control of corn planthopper (*Peregrinus maidis*) through contact and/or systemic means, the test unit consisted of a small open container with a 3-4-day-old maize plant (spike) inside. White sand was added to the top of the soil prior to application. Test compounds were formulated and sprayed at 250, 50, 10 and/or 2 ppm, and replicated three times as described for Test A. After spraying, the test units were allowed to dry for 1 h before they were post-infested with ~15-20 nymphs (18 to 21 day old) by sprinkling them onto the sand with a salt shaker. A black, screened cap was placed on the top of each test unit, and the test units were held for 6 days in a growth chamber at 22-24° C. and 50-70% relative humidity. Each test unit was then visually assessed for insect mortality.

Of the compounds of Formula 1 tested at 250 ppm the following provided very good to excellent levels of control efficacy (80% or more mortality): 1, 2, 3 and 10.

Of the compounds of Formula 1 tested at 50 ppm the following provided very good to excellent levels of control efficacy (80% or more mortality): 1, 2, 3, 4, 5, 9, 10, 11, 12, 15, 16, 17, 18 and 19.

Of the compounds of Formula 1 tested at 10 ppm the following provided very good to excellent levels of control efficacy (80% or more mortality): 1, 2, 3, 5, 10, 11, 12, 15, 16, 17 and 19.

Of the compounds of Formula 1 tested at 2 ppm the following provided very good to excellent levels of control efficacy (80% or more mortality): 2, 3 and 15.

Test E

For evaluating control of potato leafhopper (*Empoasca fabae*) through contact and/or systemic means, the test unit consisted of a small open container with a 5-6-day-old Soleil bean plant (primary leaves emerged) inside. White sand was added to the top of the soil and one of the primary leaves was excised prior to application.

Test compounds were formulated and sprayed at 250, 50, 10 and/or 2 ppm, and the tests were replicated three times as described for Test A. After spraying, the test units were allowed to dry for 1 h before they were post-infested with 5 potato leafhoppers (18-21-day-old adults). A black, screened cap was placed on the top of each test unit, and the test units were held for 6 days in a growth chamber at 24° C. and 70% relative humidity. Each test unit was then visually assessed for insect mortality.

Of the compounds of Formula 1 tested at 250 ppm the following provided very good to excellent levels of control efficacy (80% or more mortality): 1 and 3.

Of the compounds of Formula 1 tested at 50 ppm the following provided very good to excellent levels of control efficacy (80% or more mortality): 1, 2, 3, 4, 5, 6, 7, 8, 9, 10, 11, 12, 13, 15, 18 and 19.

Of the compounds of Formula 1 tested at 10 ppm the following provided very good to excellent levels of control efficacy (80% or more mortality): 1, 2, 3, 5, 6, 7, 9, 11, 12, 15 and 19.

Of the compounds of Formula 1 tested at 2 ppm the following provided very good to excellent levels of control efficacy (80% or more mortality): 1, 7 and 15.

Test F

For evaluating control of Western Flower Thrips (*Frankliniella occidentalis*) through contact and/or systemic means, the test unit consisted of a small open container with a 5-7-day-old Soleil bean plant inside.

Test compounds were formulated and sprayed at 250 ppm, and the tests were replicated three times as described for Test A. After spraying, the test units were allowed to dry for 1 hour, and then 22-27 adult thrips were added to the unit. A black, screened cap was placed on the top of each test unit, and the test units were held for 7 days at 25° C. and 45-55% relative humidity.

Of the compounds of Formula 1 tested at 250 ppm, the following provided very good to excellent levels of control efficacy (30% or less plant damage and/or 100% mortality): 1 and 4.

Test G

For evaluating control of rice green leafhopper (*Nephotettix virescens*) through contact and/or systemic means, the test unit consisted of a plastic pot containing a 13-cm-tall rice plant covered with steel wire mesh (50 mesh) supported by a wire frame. A small amount of sand was added to form a good seal between the bottom of the wire mesh, the soil surface and the top edge of the plastic pot.

Test compounds were formulated and sprayed at 50, 10 and/or 2 ppm, and the tests were replicated three times in a manner similar to the one described for Test A. After spraying, the test units were allowed to dry for 2 h before they were post-infested with 10 green leafhoppers ($3^{rd}$ instar nymphs, 7-9 days post-hatch). After 5 days, each test unit was visually assessed for insect mortality.

Of the compounds of Formula 1 tested at 50 ppm the following provided very good to excellent levels of control efficacy (80% or more mortality): 2, 3, 7, 10, 11 and 12.

Of the compounds of Formula 1 tested at 10 ppm the following provided very good to excellent levels of control efficacy (80% or more mortality): 2, 3, 7, 10 and 11.

Of the compounds of Formula 1 tested at 2 ppm the following provided very good to excellent levels of control efficacy (80% or more mortality): 3 and 7.

Test H

For evaluating control of rice brown planthopper (*Nilaparvata lugens*) through contact and/or systemic means, the test unit consisted of a plastic pot containing a 13-cm-tall rice plant covered with steel wire mesh (50 mesh) supported by a wire frame. A small amount of sand was added to form a good seal between the bottom of the wire mesh, the soil surface and the top edge of the plastic pot.

Test compounds were formulated and sprayed at 10, 2 and/or 0.4 ppm, and the tests were replicated three times in a manner similar to the one described for Test A. After spraying, the test units were allowed to dry for 2 h before they were post-infested with 10 brown planthoppers (3rd instar nymphs, 7-9 days post-hatch). After 5 days, each test unit was visually assessed for insect mortality.

Of the compounds of Formula 1 tested at 10 ppm the following provided very good to excellent levels of control efficacy (80% or more mortality): 2, 3, 7, 9, 10, 11, 12 and 15.

Of the compounds of Formula 1 tested at 2 ppm the following provided very good to excellent levels of control efficacy (80% or more mortality): 2, 3, 7 and 10.

Of the compounds of Formula 1 tested at 0.4 ppm the following provided very good to excellent levels of control efficacy (80% or more mortality): 7.

To evaluate the effect of application of a compound of the invention on the vigor of rice crops grown under outdoor conditions, Tests 1 through 0 were conducted. "a.i." refers to the amount of active ingredient applied.

Test I

Rice plants (indica cultivar 'MTU1010') were transplanted into flooded 5 m×3 m test plots of clay loam soil in the delta region of the West Godavri district, Andhra Pradesh, India, during the rainy season, and grown using local agronomic practices. After 47 days, aqueous mixtures of Compound 3 were applied to the foliage of the rice plants at 12.5, 25 or 50 g a.i./ha in a spray volume of 387 L/ha using a backpack sprayer. Plots of unsprayed rice plants were used as controls. Each treatment and control was replicated three times, and the plots were arranged in a randomized complete block design. At the time of application of Compound 3, the pest level of rice brown planthopper (*Nilaparvata lugens*) was high, i.e. much above the level considered economically significant.

The crop vigor of the rice plants in each plot was visually rated based on general external appearance (e.g., plant height) 20 days after application on a 0 to 200% scale, wherein the plants in untreated control plots were considered to represent 100%, and the results for the three replicates for each treatment were averaged. More than 100% means the plants in a treated plot were more vigorous than those in the untreated control plot, while less than 100% means the plants in the treated pot were less vigorous. The rice plants treated with 12.5, 25 and 50 g a.i./ha of Compound 3 demonstrated 140%, 143% and 143% crop vigor, respectively, compared to 100% of untreated controls.

Test J

Rice plants (indica cultivar 'MTU1010') were transplanted into flooded 5 m×3 m test plots of clay loam soil in the delta region of the West Godavri district, Andhra Pradesh, India, during the rainy season, and grown using local agronomic practices. After 52 days, aqueous mixtures of Compound 3 were applied to the foliage of the rice plants at 12.5, 25 or 50 g a.i./ha in a spray volume of 387 L/ha using a backpack sprayer. Plots of unsprayed rice plants were used as controls. Each treatment and control was replicated three times, and the plots were arranged in a randomized complete block design. At the time of application of Compound 3, the pest level of rice brown planthopper (*Nilaparvata lugens*) was high, i.e. much above the level considered economically significant. 20 days after the first treatment, the foliar applications of aqueous mixtures of Compound 3 were repeated at the same application rates in a spray volume of 467 L/ha.

The crop vigor of the rice plants in earch plot was visually rated 48 days after first application on a 0 to 200% scale as described for Test I. The rice plants treated with 12.5, 25 and 50 g a.i./ha of Compound 3 demonstrated 148%, 148% and 148% crop vigor, respectively, compared to 100% of untreated controls.

Test K

Rice plants (indica cultivar 'JAYA') were transplanted into flooded 6 m×5 m test plots of clay loam soil under shade cloth in the State of Gujarat, India during the hot season before monsoon arrival, and grown using local agronomic practices.

Accordingly, after 44 days from transplanting, all rice plants in this test were sprayed with an aqueous mixture containing 30 g a.i./ha of cypermethrin and 100 g a.i./ha of picoxystrobin. After 53 days from transplanting, aqueous mixtures of Compound 3 were applied to the foliage of the rice plants at 6.25, 12.5, 25 or 50 g a.i./ha in a spray volume of 500 L/ha using a backpack sprayer. Plots of unsprayed rice plants were used as controls. Each treatment and control was replicated three times, and the plots were arranged in a randomized complete block design. At the time of application of Compound 3, the pest level of rice brown planthopper (*Nilaparvata lugens*) was moderate, but still above the level considered economically significant.

The crop vigor of the rice plants in each plot was visually rated 32 days after application on a 0 to 200% scale as described for Test I. The rice plants treated with 6.25, 12.5, 25 and 50 g a.i./ha of Compound 3 demonstrated 115%, 113%, 122% and 115% crop vigor, respectively, compared to 100% of untreated controls.

At 45 days after application, the height and panicle length of the rice plants were measured. Plant height was determined by measuring length from vertically extended longest leaf tip to soil surface. Panicle length was measured similarly. The average height of rice plants treated with 6.25, 12.5, 25 and 50 g a.i./ha of Compound 3 was 0.94, 0.92, 0.92 and 0.99 m, respectively, compared to 0.78 m for untreated control plants. The average panicle length of rice plants treated with 6.25, 12.5, 25 and 50 g a.i./ha of Compound 3 was 23.8, 23.7, 24.9 and 24.6 cm, respectively, compared to 22.4 cm for untreated control plants. While the only treatments with Compound 3 at 25 and 50 g a.i./ha significantly increased panicle length, all the treatments substantially increased plant height.

Test L

Rice plants (indica cultivar 'IR 64') were transplanted into flooded 6 m×5 m test plots of clay loam soil in the Dhamtari district, State of Chhattisgarh, India, in the early spring season, and grown using local agronomic practices. After 79 days, in the hot season before monsoon arrival, aqueous mixtures containing 30 g a.i./ha of indoxacarb in form of STEWARD® Insecticide, 20 g a.i./ha of chlorantraniliprole, and 6.25, 12.5, 25 or 50 g a.i./ha of Compound 3 were applied to the foliage of the rice plants at in a spray volume of 500 L/ha using a backpack sprayer. Plots of control rice plants were sprayed with an aqueous mixture containing 30 g a.i./ha of indoxacarb in form of STEWARD® Insecticide and 20 g a.i./ha of chlorantraniliprole (i.e. no Compound 3). Each treatment and control was replicated three times, and the plots were arranged in a randomized complete block design. At the time of application of Compound 3, the pest level of rice brown planthopper (*Nilaparvata lugens*) was high, i.e. above the level considered economically significant.

The crop vigor of the rice plants in each plot was visually rated 21 days after application on a 0 to 200% scale as described for Test I. At all application rates the treated rice plants showed the same level of crop vigor (i.e. 100%) as untreated control plants. Even though the pest level was high, at the time of treatment the plants had already reached full height and produced panicles, so the treatment with Compound 3 was too late to noticeably increase crop vigor rated by general external appearance (e.g., plant height, number of panicles). Nevertheless, the treatments substantially benefited crop vigor as measured by harvest yield. Harvest yields from the crops treated with 6.25, 12.5, 25 and 50 g a.i./ha of Compound 3 were 4630, 4830, 4730 and 4930 kg/ha, respectively, compared to 2630 kg/ha from the untreated controls. Therefore even the late treatments substantially increased crop yield by preventing planthopper damage that would otherwise stop the process of grain filling, resulting in empty panicles.

Test M

Rice plants (indica cultivar) were direct seeded into flooded 6 m×5 m test plots of clay loam soil in An Giang Province of Vietnam shortly before the monsoon, and grown using local agronomic practices. After 42 days, at the beginning of the wet season, aqueous mixtures containing 30 g a.i./ha of indoxacarb in form of STEWARD® Insecticide, 20 g a.i./ha of chlorantraniliprole, and 6.25, 12.5, 25 or 50 g a.i./ha of Compound 3 were applied to the foliage of the rice plants at in a spray volume of 400 L/ha using a motorized sprayer. Plots of control rice plants were sprayed with an aqueous mixture containing 30 g a.i./ha of indoxacarb in form of STEWARD® Insecticide and 20 g a.i./ha of chlorantraniliprole (i.e. no Compound 3). Each treatment and control was replicated three times, and the plots were arranged in a randomized complete block design. At the time of application of Compound 3, the pest level of rice brown planthopper (*Nilaparvata lugens*) was very low.

The crop vigor of the rice plants in each plot was visually rated 18 days after application on a 0 to 200% scale as described for Test I. At all application rates the treated rice plants showed the same level of crop vigor (i.e. 100%) as untreated control plants. Because the pest level was very low and growing conditions were ideal, applications of Compound 3 did not noticeably increase plant vigor.

Test N

Rice plants (indica cultivar 'Swarna') were transplanted into flooded 4 m×3 m test plots of clay loam soil in the Bargarh district, Orissa, India, during the rainy season, and grown using local agronomic practices. After 70 days, aqueous mixtures of Compound 3 were applied to the foliage of the rice plants at 12.5, 25 or 50 g a.i./ha in a spray volume of 400 L/ha using a backpack sprayer. Plots of unsprayed rice plants were used as controls. Each treatment and control was replicated three times, and the plots were arranged in a randomized complete block design. At the time of application of Compound 3, the pest level of rice brown planthopper (*Nilaparvata lugens*) was high, i.e. much above the level considered economically significant. 14 days after the first treatment, the foliar applications of aqueous mixtures of Compound 3 were repeated at the same application rates in a spray volume of 400 L/ha.

Harvest yields from the crops treated with 12.5, 25 and 50 g a.i./ha of Compound 3 were 3190, 3660 and 4220 kg/ha, respectively, compared to 620 kg/ha from the untreated controls.

Test O

Rice plants (indica cultivar 'IR-64') were transplanted into flooded 5 m×5 m test plots of clay loam soil the Bargarh district, Orissa, India, at the end of the winter season, and grown using local agronomic practices. After 79 days, aqueous mixtures containing 30 g a.i./ha of indoxacarb in form of STEWARD® Insecticide, 20 g a.i./ha of chlorantraniliprole, and 6.25, 12.5, 25 or 50 g a.i./ha of Compound 3 were applied to the foliage of the rice plants at in a spray volume of 500 L/ha using a backpack sprayer. Plots of control rice plants were sprayed with an aqueous mixture containing 30 g a.i./ha of indoxacarb in form of STEWARD® Insecticide and 20 g a.i./ha of chlorantraniliprole (i.e. no Compound 3). Each treatment and control was replicated three times, and the plots were arranged in a randomized complete block design. At the time of application of Compound 3, the pest level of rice brown planthopper (*Nilaparvata lugens*) was high, i.e. much above the level considered economically significant.

Harvest yields from the crops treated with 12.5, 25 and 50 g a.i./ha of Compound 3 were 2470, 3430, 3470 and 4600 kg/ha, respectively, compared to 1370 kg/ha from the untreated controls.

Test P

In this test, the effect of a compound of the invention on the vigor of maize plants grown in a greenhouse in absence of pest pressure was measured.

Single maize seeds (Prairie Hybrid 2431 organic field corn) were planted 2.0 to 2.5 cm deep in 10 cm×10 cm×8 cm plastic pots containing either Redi-Earth sphagnum peat moss-based potting media (Sun Gro Horticulture Canada Ltd., Vancouver, British Columbia) or a 50/50 mixture of Matapeake soil and sand. Seeded pots were initially watered to a 5 cm depth and placed in a growth chamber maintained at 25° C. within a 16 h light/8 h dark photoperiod. The pots were watered whenever the soil surface dried.

After 8 days from initial watering, the potted plants were treated by applying as a surface drench 40 mL of an aqueous treatment mixture containing either 0.2 or 2.5 mg of Compound 3. To the pots of untreated control plants, 40 mL of tap water was similarly applied. Treatments and untreated controls were replicated 10 times.

Treated and untreated plants were then arranged in a complete randomized block design in a greenhouse maintained at 25.6-27.8° C. during the day and 23.0-25.0° C. at night. Supplemental lighting was added when outside light levels dropped below 200 watts m$^{-2}$ during a 16-h growing period, except that no supplemental lighting was activated when outside light energy had already accumulated to more than 5000 w h m$^{-2}$ during the growing period. Greenhouse shading closed when outside light levels rose above 600 watts m$^{-2}$ for for more than 20 minutes.

No modifications to relative humidity were made. Tap water irrigation was provided twice daily as needed to maintain soil moisture. Every second or third day the plants were fertilized with irrigation water containing 100 ppm N—P—K from Peters® soluble 20-20-20 general purpose fertilizer (The Scotts Company, Marysville, Ohio, U.S.A.). The applied nutrient levels were considered less that ideal for optimal growth of maize plants.

Plant height was determined at 0, 7, 14, 21 and 28 days after treatment by measuring the length from the vertically extended longest leaf tip to the soil surface. The heights averaged across the 10 replicates are listed in Test Tables 1 and 2 for plants grown in Redi-Earth soil and Matapeake Soil/Sand, respectively.

TEST TABLE 1

Effect of Treatments with Compound 3 on Heights of Maize Plants Grown on Redi-Earth Soil

| Application Rate (mg a.i./pot) | Height (cm) at Days after Treatment | | | | |
|---|---|---|---|---|---|
| | 0 days | 7 days | 14 days | 21 days | 28 days |
| 0 | 21 | 52 | 84 | 109 | 133 |
| 0.2 | 22 | 53 | 85 | 111 | 131 |
| 2.5 | 21 | 53 | 85 | 111 | 137 |

TEST TABLE 2

Effect of Treatments with Compound 3 on Heights of Maize Plants Grown in Matapeake Soil/Sand

| Application Rate (mg a.i./pot) | Height (cm) at Days after Treatment | | | | |
|---|---|---|---|---|---|
| | 0 days | 7 days | 14 days | 21 days | 28 days |
| 0 | 22 | 49 | 66 | 78 | 89 |
| 0.2 | 22 | 49 | 66 | 76 | 87 |
| 2.5 | 22 | 46 | 65 | 78 | 88 |

The results in Test Tables 1 and 2 show that little growth enhancing effect was noticeable from applications of Compound 3 to maize plants grown in a pest-free environment under growing conditions that were close to ideal except for being nutrient constrained.

What is claimed is:

1. The compound N-[(5-pyrimidinyl)methyl]-2-pyridinamine.

2. The compound N-(5-pyrimidinylmethylene)-2-pyridinamine.

\* \* \* \* \*